(12) United States Patent
Selvaraj et al.

(10) Patent No.: US 11,873,481 B2
(45) Date of Patent: Jan. 16, 2024

(54) PRESERVING SPATIAL-PROXIMAL CONTIGUITY AND MOLECULAR CONTIGUITY IN NUCLEIC ACID TEMPLATES

(71) Applicant: ARIMA GENOMICS, INC., San Diego, CA (US)

(72) Inventors: Siddarth Selvaraj, San Diego, CA (US); Anthony Schmitt, Poway, CA (US); Bret Reid, San Diego, CA (US)

(73) Assignee: Arima Genomics, Inc., Carlsbad, CA (US)

( * ) Notice: Subject to any disclaimer, the term of this patent is extended or adjusted under 35 U.S.C. 154(b) by 445 days.

(21) Appl. No.: 16/764,787

(22) PCT Filed: Nov. 20, 2018

(86) PCT No.: PCT/US2018/062005
§ 371 (c)(1),
(2) Date: May 15, 2020

(87) PCT Pub. No.: WO2019/104034
PCT Pub. Date: May 31, 2019

(65) Prior Publication Data
US 2021/0363516 A1 Nov. 25, 2021

Related U.S. Application Data

(60) Provisional application No. 62/589,505, filed on Nov. 21, 2017.

(51) Int. Cl.
*C12N 15/10* (2006.01)
*C12Q 1/6869* (2018.01)

(52) U.S. Cl.
CPC ....... *C12N 15/1065* (2013.01); *C12Q 1/6869* (2013.01)

(58) Field of Classification Search
None
See application file for complete search history.

(56) References Cited

U.S. PATENT DOCUMENTS

| 8,642,295 B2 | 2/2014 | De Laat et al. |
| 9,273,309 B2 | 3/2016 | Dekker et al. |

(Continued)

FOREIGN PATENT DOCUMENTS

| WO | 2015010051 A1 | 1/2015 |
| WO | 2015123588 A1 | 8/2015 |

(Continued)

OTHER PUBLICATIONS

Adey et al., "In vitro, long-range sequence information for de novo genome assembly via transposase contiguity," Genome Res. 2014, 24:2041-2049. (Year: 2014).*

(Continued)

*Primary Examiner* — Kaijiang Zhang
(74) *Attorney, Agent, or Firm* — Wolf, Greenfield & Sacks, P.C.

(57) ABSTRACT

Provided herein are methods and compositions for preparing nucleic acid templates wherein spatial-proximal and molecular contiguity of target nucleic acids is preserved, and the sequencing data obtained therefrom is used, but not limited to, identification of genomic variants, determination of contiguity information to inform assemblies of target nucleic acids de novo including deconvolution of haplotype phase information, and analyses of conformation and topology of target nucleic acids.

18 Claims, 23 Drawing Sheets

(56) References Cited

U.S. PATENT DOCUMENTS

| | | | |
|---|---|---|---|
| 9,434,985 | B2 | 9/2016 | Dekker et al. |
| 9,688,981 | B2 | 6/2017 | Dekker et al. |
| 9,708,648 | B2 | 7/2017 | Dekker et al. |
| 2011/0287947 | A1 | 11/2011 | Chen et al. |
| 2013/0183672 | A1 | 7/2013 | De Laat et al. |
| 2014/0045705 | A1 | 2/2014 | Bustamante et al. |
| 2015/0225786 | A1 | 8/2015 | Litterst et al. |
| 2016/0160275 | A1 | 6/2016 | Ren et al. |
| 2016/0194710 | A1* | 7/2016 | Aiden et al. ............. C12Q 1/68 435/6.12 |
| 2016/0239602 | A1 | 8/2016 | Shendure et al. |
| 2017/0159109 | A1* | 6/2017 | Zheng et al. ........ C12Q 1/6806 |
| 2017/0362649 | A1 | 12/2017 | Lieberman-Aiden et al. |
| 2018/0245069 | A1 | 8/2018 | Desantis et al. |

FOREIGN PATENT DOCUMENTS

| | | | |
|---|---|---|---|
| WO | 2016061517 | A2 | 4/2016 |
| WO | 2017004612 | A1 | 1/2017 |
| WO | 2017068379 | A1 | 4/2017 |
| WO | 2017090543 | A1 | 6/2017 |
| WO | 2017197300 | A1 | 11/2017 |
| WO | 2019104034 | A1 | 5/2019 |

OTHER PUBLICATIONS

Nagano et al., "Comparison of Hi-C results using in-solution versus in-nucleus ligation," Genome Biol. 2015, 16:175. (Year: 2015).*

Genome Reagent Kits v2 User Guide, 10x Genomics, 75 pages.

International Preliminary Report on Patentability dated Jun. 4, 2020 in International Patent Application No. PCT/US2018/062005, filed on Nov. 20, 2018, 10 pages.

International Search Report and Written Opinion Received dated May 7, 2019 in International Patent Application No. PCT/US2018/062005, filed on Nov. 20, 2018, 18 pages.

Adey et al., "In Vitro, Long-Range Sequence Information for De Novo Genome Assembly via Transposase Contiguity", Genome Research, 2014, 24:2041-2049.

Adey et al., "Rapid, Low-Input, Low-Bias Construction of Shotgun Fragment Libraries by High-Density in Vitro Transposition", Genome Biology, 2010, 11:R119:17 pages.

Amini et al., "Haplotype-Resolved Whole Genome Sequencing by Contiguity Preserving Transposition and Combinatorial Indexing", Nature Genetics, Oct. 19, 2014, 9 pages.

Beitel et al., "Strain- and Plasmid-Level Deconvolution of a Synthetic Metagenome by Sequencing Proximity Ligation Products", PeerJ, 2014, 2(12):e415.

Bickhart et al., "Single-Molecule Sequencing and Chromatin Conformation Capture Enable De Novo Reference Assembly of the Domestic Goat Genome", Nature Genetics, Apr. 2017, 49(4):643-650.

Burton et al., "Chromosome-Scale Scaffolding of De Novo Genome Assemblies Based on Chromatin Interactions", Nature Biotechnology, Dec. 2013, 31(12):1119-1125.

Burton et al., "Species-Level Deconvolution of Metagenome Assemblies with Hi-C-Based Contact Probability Maps", G3: Genes, Genomes, Genetics, doi: 10.1534/g3.114.011825., Jul. 2014, 4(7):1339-1346.

Comet et al., "A Chromatin Insulator Driving Three-Dimensional Polycomb Response Element (PRE) Contacts and Polycomb Association with the Chromatin Fiber", Proceedings of the National Academy of Sciences, Feb. 8, 2011, 108(6):2294-2299.

Compeau et al., "How to apply de Bruijn graphs to genome assembly", Nature Biotechnology, Nov. 2011, 29(11):987-991.

Cremer et al., "Chromosome Territories", Cold Spring Harbor Perspectives in Biology, a003889, 2010, 2:22 pages.

Dekker et al., "Capturing Chromosome Conformation", Science, Feb. 15, 2002, 295(5558):1306-1311.

Depristo et al., "A Framework for Variation Discovery and Genotyping Using Next-Generation DNA Sequencing Data", Nature Genetics, May 2011, 43(5):491-498.

Dostie et al., "Chromosome Conformation Capture Carbon Copy (5C): A Massively Parallel Solution for Mapping Interactions Between Genomic Elements", Genome Research, Oct. 2006, 16(10):1299-1309.

Dudchenko et al., "De Novo Assembly of the Aedes Aegypti Genome Using Hi-C Yields Chromosome-Length Scaffolds", Science, Apr. 7, 2017, 356:92-95.

Eberle et al., "A Reference Data Set of 5.4 Million Phased Human Variants Validated by Genetic Inheritance from Sequencing a Three-Generation 17-Member Pedigree", Genome Research, 2016, 27(1):157-164.

Edge et al., "HapCUT2: Robust and Accurate Haplotype Assembly for Diverse Sequencing Technologies", Genome Research, 2016, 27:801-812.

Ferhat et al., "Identifying Multi-Locus Chromatin Contacts in Human Cells Using Tethered Multiple 3C", BMC Genomics, 2015, 16(121):17 pages.

Gnirke et al., "Solution Hybrid Selection with Ultra-Long Oligonucleotides for Massively Parallel Targeted Sequencing", Nature Biotechnology, Feb. 2009, 27(2):182-189.

Hayden Erika Check, "Technology: The $1,000 Genome", Nature, Mar. 20, 2014, 507:294-295.

Kalhor et al., "Genome Architectures Revealed by Tethered Chromosome Conformation Capture and Population-Based Modeling", Nature Biotechnology, 2012, 30(1):90-98.

Kaplan et al., "High-Throughput Genome Scaffolding from In-Vivo DNA Interaction Frequency", Nature Biotechnology, 2013, 31(12):1143-1147.

Kayser et al., "Improving Human Forensics Through Advances in Genetics, Genomics and Molecular Biology", Nature Reviews Genetics, Mar. 2011, 12(3):179-192.

Lander et al., "Initial Sequencing and Analysis of the Human Genome", Nature, Feb. 15, 2001, 409:860-921.

Lieberman-Aiden et al., "Comprehensive Mapping of Long-Range Interactions Reveals Folding Principles of the Human Genome", Science, Oct. 2009, 326(5950):289-293.

Mckenna et al., "The Genome Analysis Toolkit: A MapReduce Framework for Analyzing Next-Generation DNA Sequencing Data", Genome Research, 2010, 20:1297-1303.

Nagano et al., "Comparison of Hi-C Results using in-Solution Versus In-Nucleus Ligation", Genome Biology, 2015, 16(175):26 pages.

Nagano et al., "Single Cell Hi-C Reveals Cell-To-Cell Variability in Chromosome Structure", Nature, Oct. 2013, 502(7469):59-64.

Naumova et al., "Analysis of Long-Range Chromatin Interactions Using Chromosome Conformation Capture", Methods, Nov. 2012, 58(3):27 pages.

Padmanabhan et al., "Genomics and Metagenomics in Medical Microbiology", Journal of Microbiological Methods, 2013, 95:415-424.

Rao et al., "A 3D Map of the Human Genome at Kilobase Resolution Reveals Principles of Chromatin Looping", Cell, Dec. 18, 2014, 159:1665-1680.

Ronald Pamela C., "Lab to Farm: Applying Research on Plant Genetics and Genomics to Crop Improvement", PLOS Biology, e1001878, Jun. 2014, 12(6):6 pages.

Selvaraj et al., "Complete Haplotype Phasing of the MHC And KIR Loci with Targeted Haploseq", BMC Genomics, doi: 10.1186/s12864-015-1949-7, 2015, 16(900):7 pages.

Selvaraj et al., "Whole-Genome Haplotype Reconstruction Using Proximity-Ligation and Shotgun Sequencing", Nature Biotechnology, doi: 10.1038/nbt.2728, 2013, 31(12):1111-1118.

Shendure et al., "The Expanding Scope of DNA Sequencing", Nature Biotechnology, Nov. 2012, 30(11):1084-1094.

Simonis et al., "Nuclear Organization of Active and Inactive Chromatin Domains Uncovered by Chromosome Conformation Capture-On-Chip (4C)", Nature Genetics, Nov. 2006, 38(11)1348-1354.

Soler et al., "The Genome-Wide Dynamics of the Binding of Ldb1 Complexes During Erythroid Differentiation", Genes & Development, 2010, 24:277-289.

(56) References Cited

OTHER PUBLICATIONS

Stadhoulders et al., "Dynamic Long-Range Chromatin Interactions Control Myb Proto-Oncogene Transcription During Erythroid Development", The EMBO Journal, 2012, 31:986-999.
Tolhuis et al., "Looping and Interaction Between Hypersensitive Sites in the Active Beta-Globin Locus", Molecular Cell, Dec. 2002, 10:1453-1465.
Troll et al., "Structural Variation Detection by Proximity Ligation from Formalin-Fixed, Paraffin-Embedded Tumor Tissue", The Journal of Molecular Diagnostics, May 2019, 21(3):375-383.
Venter et al., "The Sequence of the Human Genome", Science, Feb. 16, 2001, 291(5507):1304-1351.
Wang et al., "Genomics and Drug Response", The New England Journal of Medicine, Mar. 2011, 364(12):1144-1153.
Weisenfeld et al., "Direct Determination of Diploid Genome Sequences", Genome Research, May 13, 2017, 27:1-11.
Williamson et al., "Spatial Genome Organization: Contrasting Views from Chromosome Conformation Capture and Fluorescence in Situ Hybridization", Genes & Development, 2014, 28:2778-2791.
Yang et al., "Application of Next-generation Sequencing Technology in Forensic Science", Genomics Proteomics & Bioinformatics, 2014, 12(5):190-197.
Zhang et al., "Haplotype Phasing of Whole Human Genomes Using Bead-Based Barcode Partitioning in a Single Tube", Nature Biotechnology, Sep. 2017, 35(9):852-857.
Zheng et al., "Haplotyping Germline and Cancer Genomes with High-Throughput Linked-Read Sequencing", Nature Biotechnology, Mar. 2016, 34(3):303-311.
Zook et al., "Extensive Sequencing of Seven Human Genomes to Characterize Benchmark Reference Materials", Scientific Data, Jun. 7, 2016, 3(160025):26 pages.

\* cited by examiner

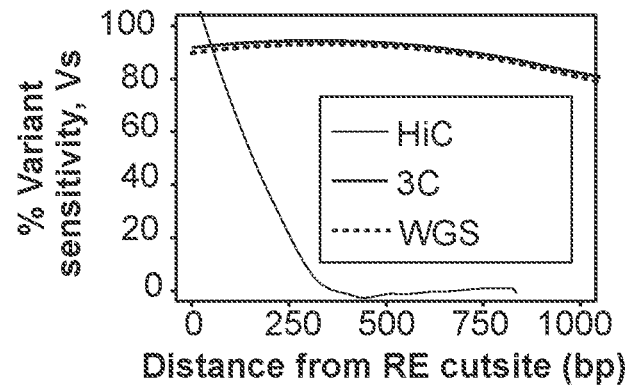
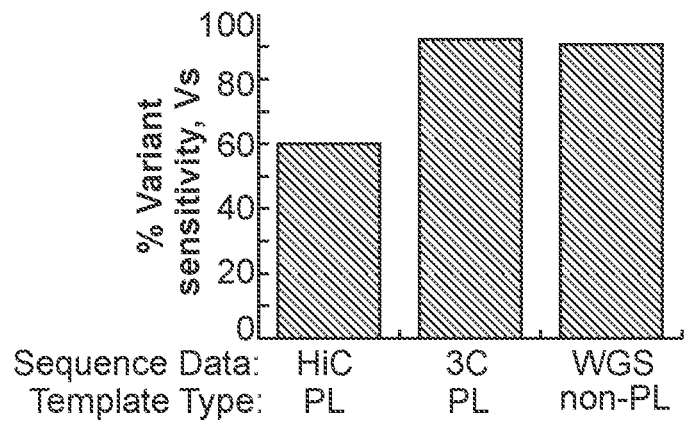
FIG. 5

Limited Haplotype phasing capability in sequence data from PL templates
(i) Chromosome-span haplotypes in sequence data from 3C and HiC templates
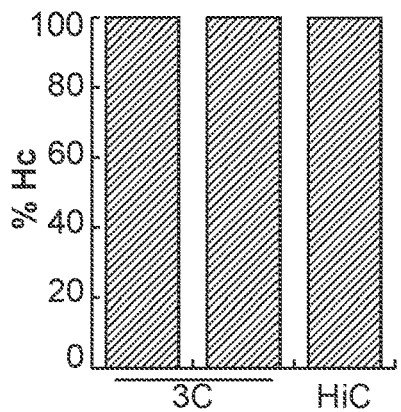
(ii) Limited Hr in sequence data from 3C and HiC templates
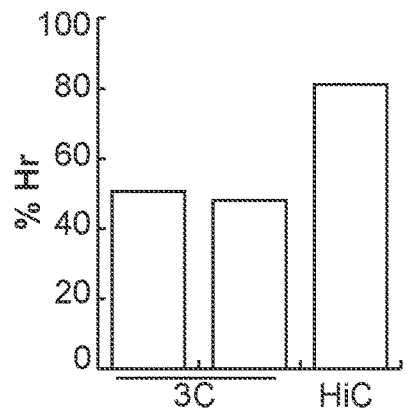
(iii) Limited Ha in sequence data from 3C and HiC templates
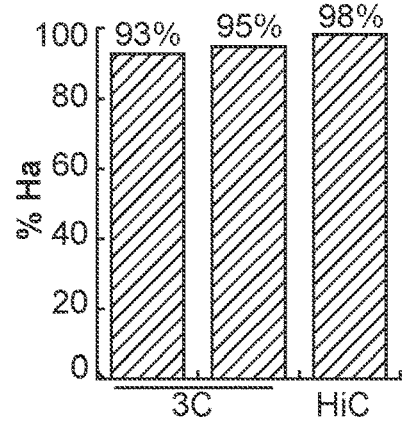
FIG. 6

Preserving spatial-proximal and molecular contiguity in PL templates can improves haplotype phasing
(i) longer PL templates preserve more haplotype phasing information
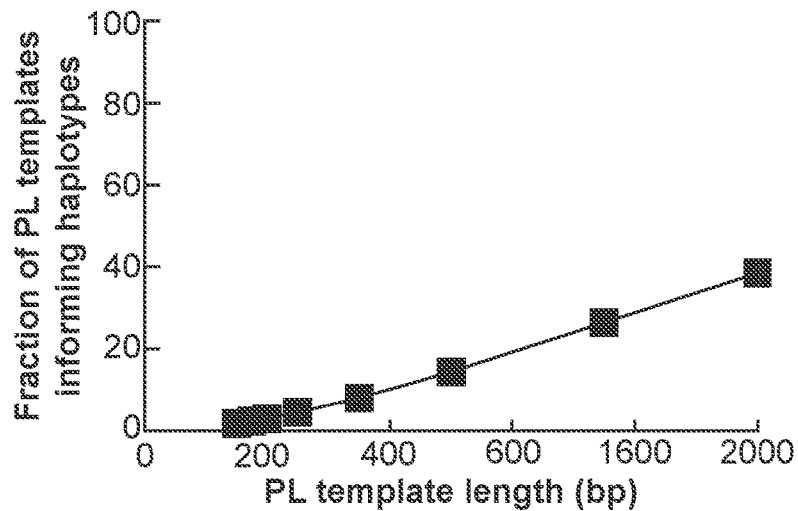
FIG. 7
(ii) longer PL templates enable improved haplotype phasing
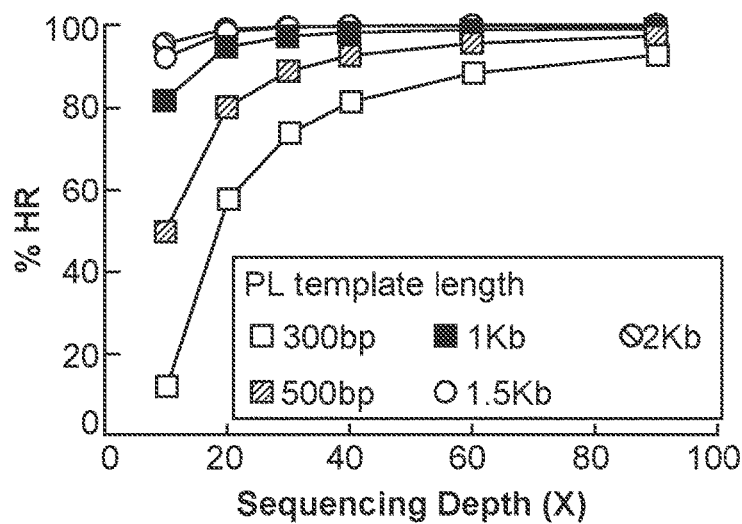

Mathematical demonstration of improved Ha due to preservation of both spatial-proximal and molecular contiguity in PL templates chr6 32,449,000 | 188 | 298 // 811 | 975 // 32,452,000 | 308

(i) *Fragmented LP based haplotyping*

HiC: G A ... HiC phasing error ... A / a g ... t

Assuming HiC read support for haplotype phasing are as follows:
$r(Gt) = 0.95$  $r(gA) = 0.92$  $r(AA) = 0.90$
P(HiC reads/H1=GAt, H2=agA) = 0.95*0.92*0.1 = 0.0874
P(HiC reads/H1=GAA, H2=agt) = 0.05*0.08*0.9 = 0.0036

3C: G A  C T    A
    a g  a c    t

G A  C T  3C phasing error  A
a g  a c ........................ t (ii) *CPSP-Prep based haplotyping* step1: G A  C T    A
       a g  a c    t

Preserving molecular contiguity improves Ha
$r(Gt) = 0.95$  $r(gA) = 0.92$  $r(AA) = 0.90$
$r(GC) = 0.80$  $r(ct) = 0.95$  $r(TA) = 0.91$ P(CPSP-seq reads/H1=GACTt, H2=agacA) = 0.0874*0.8*0.05*0.09
= 0.00031

P(CPSP-seq reads/H1=GACTA, H2=agact) = 0.0036*0.8*0.95*0.91
= 0.00248

FIG. 8

Limited preservation of spatial-proximal contiguity in nucleic acid templates
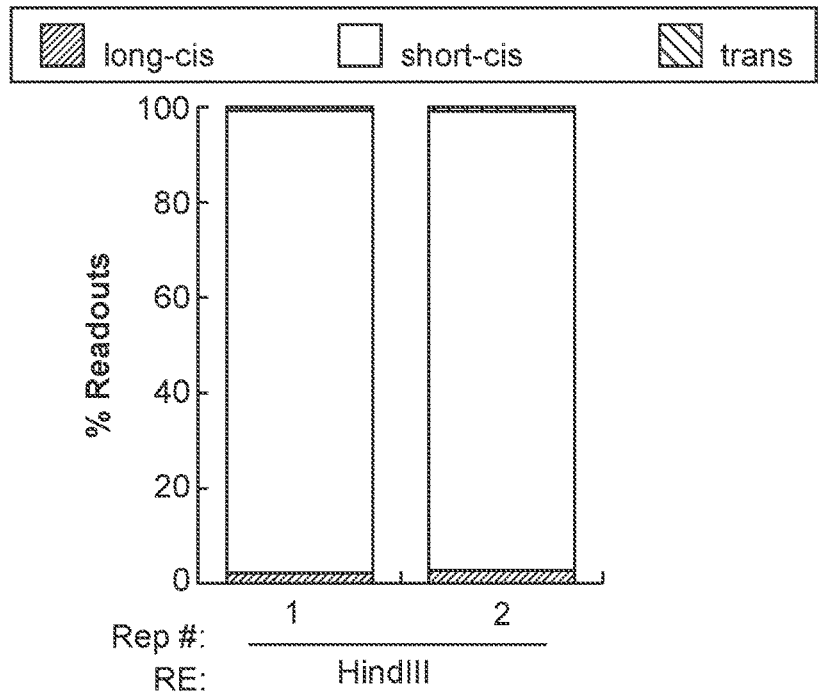
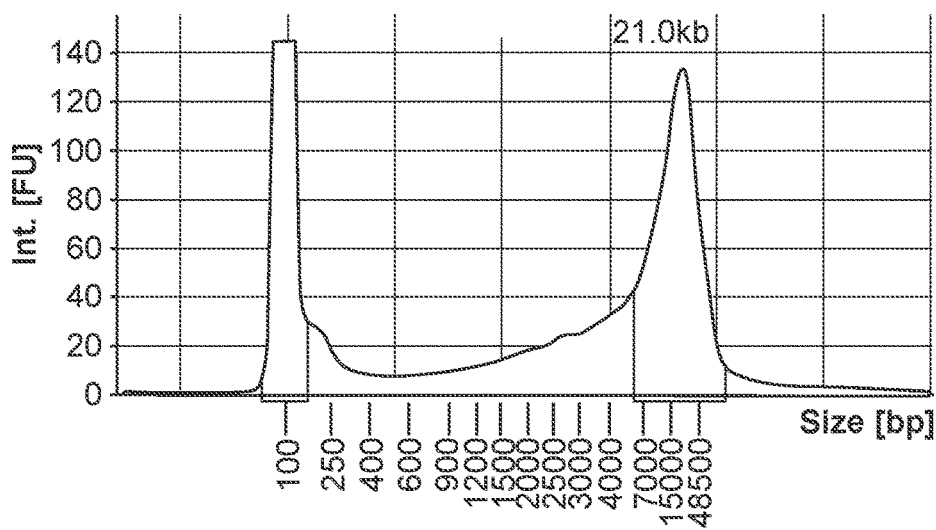
FIG. 10

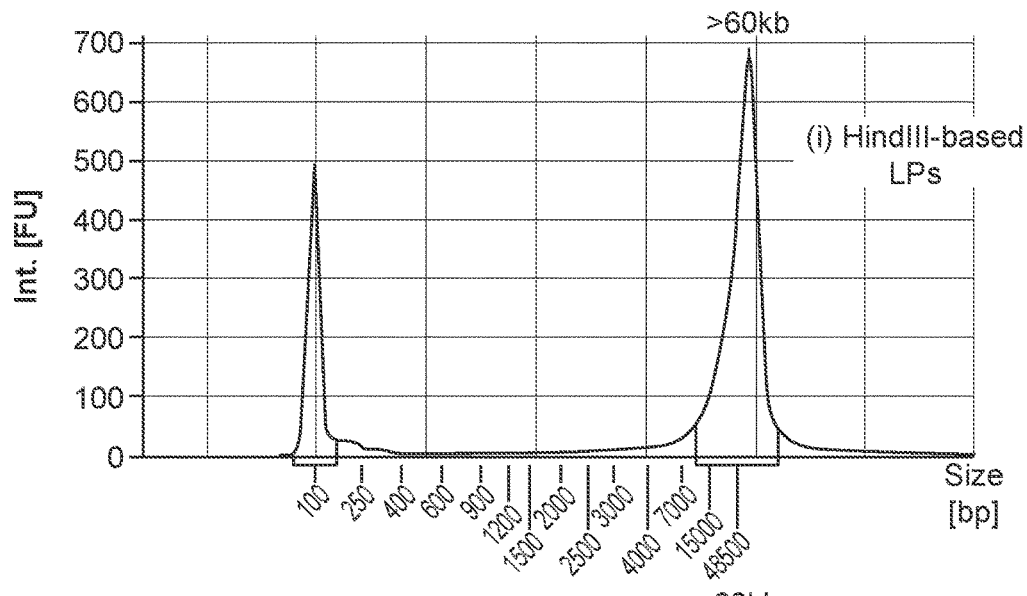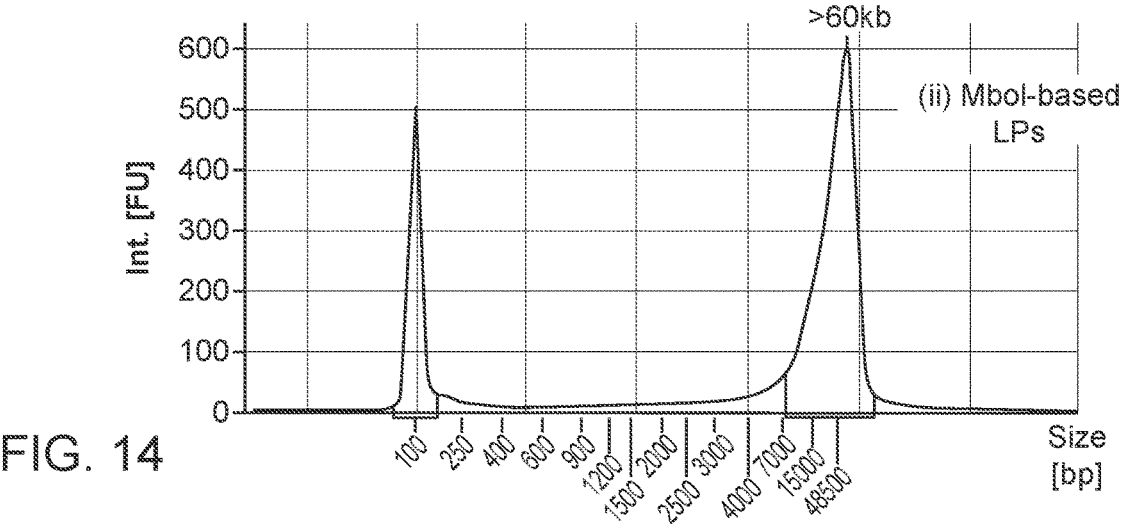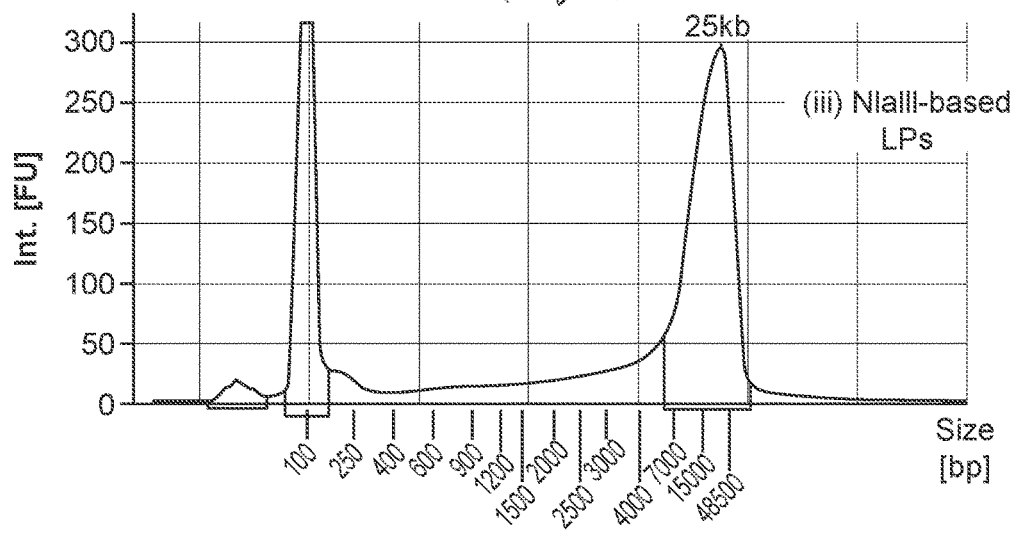
FIG. 14

Innovations towards optimizing tagging yield obtained from tagging LPs from PL methods in CPSP-Prep via RE and tagging duration optimizations
(i) Tagging Yield Solution A - Different RE in PL method
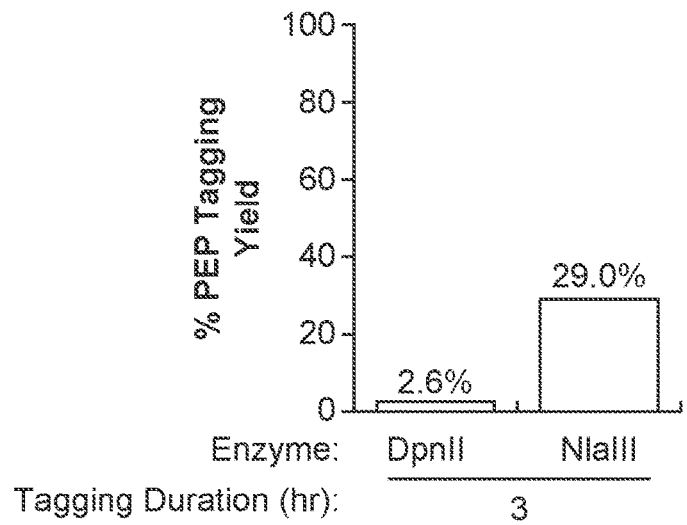
(ii) Tagging Yield Solution B - PEP tagging yield from LPs is improved by longer tagging duration
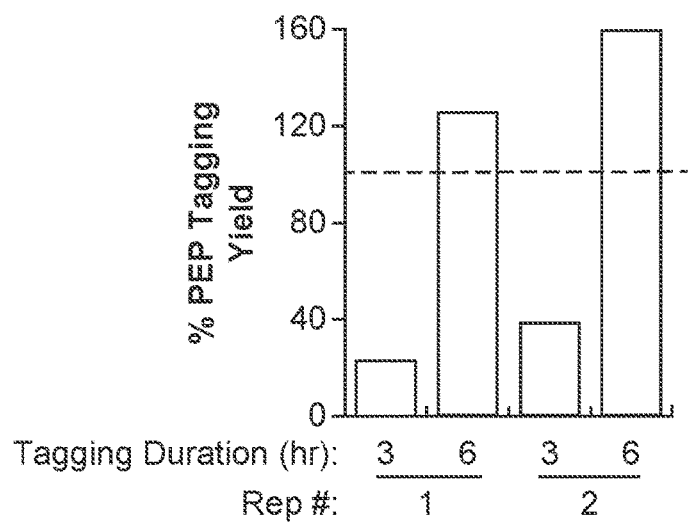
FIG. 19

PRESERVING SPATIAL-PROXIMAL CONTIGUITY AND MOLECULAR CONTIGUITY IN NUCLEIC ACID TEMPLATES

RELATED PATENT APPLICATIONS

This patent application is a 35 U.S.C. 371 national phase patent application of PCT/US2018/062005, filed on Nov. 20, 2018, entitled PRESERVING SPATIAL-PROXIMAL CONTIGUITY AND MOLECULAR CONTIGUITY IN NUCLEIC ACID TEMPLATES, naming Siddarth Selvaraj, Anthony Schmitt and Bret Reid as inventors, which claims the benefit of U.S. Provisional Patent Application No. 62/589,505 filed Nov. 21, 2017, entitled PRESERVING SPATIAL-PROXIMAL CONTIGUITY AND MOLECULAR CONTIGUITY IN NUCLEIC ACID TEMPLATES, naming Siddarth Selvaraj, Anthony Schmitt and Bret Reid as inventors. This patent application is related to U.S. Provisional Application filed Nov. 20, 2018, entitled METHODS FOR PREPARING NUCLEIC ACIDS THAT PRESERVE SPATIAL-PROXIMAL CONTIGUITY INFORMATION, naming Anthony Schmitt, Catherine Tan, Derek Reid, Chris De La Torre and Siddarth Selvaraj as inventors. The entire content of the foregoing patent applications are incorporated herein by reference, including all text, tables and drawings.

FIELD

This technology relates to sequencing nucleic acids. Specifically relating to preparing nucleic acid templates comprising nucleic acids for which spatial-proximal contiguity and molecular contiguity has been preserved to determine the nucleic acid sequence therefrom, which can be adapted for whole-genome and targeted nucleic acid sequence determination.

BACKGROUND

Next-generation sequencing (NGS) has emerged as the predominant set of methods for determining nucleic acid sequence for a plethora of research and clinical applications[1-9]. The typical NGS workflow is as follows: the native genomic DNA, often organized as chromosome(s), is isolated from the nucleic acid source leading to its fragmentation, to produce nucleic acid templates which are subsequently read by a sequencing instrument to generate sequence data. The predominant sequencing instruments read highly fragmented nucleic acid templates (e.g. Illumina sequencers read 100-500 bp).

One approach to capture contiguity during nucleic acid template preparation is by using the principle that, within nuclei, nucleic acids are often arranged in spatial conformations[10,11]. Because natively occurring spatially proximal nucleic acid molecules (nSPNAs, see definition below) can be linearly distal, capturing nSPNAs informs one form of contiguity. Indeed, methods that capture such conformation information (e.g. 3C[12], 4C[13,14], 5C[15,16], Hic[17,18], TCC[19,20], or other methods or combination of methods) capture nSPNAs and inform contiguity by "ligating" them—specifically, nSPNAs are ligated to generate ligated products (LP) of nucleic acids and the plurality of such LPs are subsequently fragmented and prepared as contiguity-preserved nucleic acid templates that are sequenced to obtain contiguity-preserved sequencing data.

SUMMARY

The method for generating contiguity-preserved nucleic acid templates disclosed herein, CPSP-Prep, involves two key steps: First, nSPNAs are captured to obtain spatial proximal information, (e.g. via PL methods or SSPC method (defined below)) and second, the spatial-proximal and the molecular contiguity within the captured nSPNAs (captured nSPNAs are hereafter referred to as cSPNAs, see definition below) is preserved, leading to the preparation of a contiguity-preserved nucleic acid template. Sequencing data (CPSP-Seq) obtained from CPSP-Prep of nucleic acid templates enables comprehensive determination of nucleic acid sequence by enabling identification of genomic variants, determination of contiguity information to inform genome assemblies de novo, deconvolution of haplotype phase information, and also facilitates analyses of conformation and topology of target nucleic acids.

DEFINITIONS

Sequencing: Unless otherwise noted, sequencing herein refers to short-read sequencing (e.g. Illumina) that sequences nucleic acid templates comprising nucleic acid fragments of lengths approximately 500 bp.

Spatially proximal nucleic acid molecules (SPNAs): Within cells, nucleic acids are often natively arranged in spatial configurations, referred herein as nSPNAs. nSPNAs are nucleic acid molecules that are in spatial proximity with each other, and when captured using a PC method (defined below), the resulting captured nSPNA, are herein referred as cSPNAs.

Proximity-Capture (PC): PC methods compromise of methodologies involving the capture of nSPNAs to result cSPNAs. "Capture" in this context comprises mechanisms that inform spatial proximity of nucleic acids.

Proximity ligation (PL): Within the PC methods, a modality of PC is the class of methodologies comprising proximity ligation (PL). A PL method is one in which nSPNAs are captured by ligation to generate ligated products (LP) (e.g. 3C, 4C, 5C, HiC, TCC, or other methods or combination of methods[12,13,15,17,19]. Proximity ligation (PL) is understood to include in situ ligation and in solution ligation. Often in a PL method, the nSPNAs from the nucleic acid source (cell(s), or, nuclei, or, nuclear matrix) are digested via use of restriction enzyme (RE) or other means of digestion, and then the digested nSPNAs are captured via ligation to form ligation products (LPs). LPs are then fragmented into shorter nucleic acids molecules and prepared as nucleic acid templates for sequencing (FIG. 2). Of note, LPs are defined to have high molecular length ranging from <1 Kb to >60 Kb and unless otherwise noted, we assume LPs to be characterized by high molecular length. Also, LPs are often depicted as circularized nucleic acid molecules (FIG. 2), but LPs can be linear or circular (FIG. 3). Also, the nucleic acids that comprise the ligation within the LP is defined as a ligation junction (LJ), and importantly, LPs are often illustrated to manifest two LJs (FIG. 3*i*), but LPs can manifest ≥2 Us as a result of multiple nSPNAs ligating together (FIG. 3*v*). Further, PL methods may also manifest unligated products (uLP) due to steric or physical constraints of nucleic acid conformation, or due to molecular biology inefficiencies, and therefore unlike uLPs, the LPs that manifest Us inform spatial-proximal contiguity. Finally, in some PL methods (e.g. HiC, FIG. 2), LJs are marked to generate MLPs (marked LPs) to deplete uLPs. To generalize, all PL workflows capture nSPNAs to generate LPs, and unless otherwise noted, the term LP incorporates MLPs and other configurations of LPs that manifest Us, except uLP. Because of this generalization, LPs can be assumed to manifest LJs.

Solid substrate-mediated proximity capture (SSPC): A new class of PC methodologies disclosed herein is termed solid substrate-mediated proximity capture (SSPC). These methodologies comprise of introducing an exogenous solid substrate that facilitates the capture of nSPNAs by virtue of the solid substrate binding to nSPNAs. Once nSPNAs are captured via binding to the solid substrate, the collection of cSPNAs bound to the solid substrate are referred to as SSPC products. Additionally, SSPC products are defined to have high molecular length ranging from <1 Kb to >60 Kb and unless otherwise noted, we assume SSPC products to be characterized by high molecular length. In sum, LPs and SSPC products represent distinct forms of cSPNAs.

Throughout the application, definitions such as cSPNAs, LPs and SSPC products can be used inter-exchangeable. Specifically cSPNAs are a generalization and can represent LP or MLP products from PL methods, or SSPC products from SSPC methods. In addition, while definitions discussed above involve methods for capturing nSPNAs to generate cSPNAs ($1^{st}$ step of CPSP-Prep), the following definitions discuss concepts for preserving spatial-proximal and molecular contiguity in the nucleic acid templates prepared from the cSPNAs ($2^{nd}$ step of CPSP-Prep).

Compartmentalizing: Regardless of whether nSPNAs are captured via PL or SSPC methods, an approach to preserve spatial-proximal and molecular contiguity within cSPNAs can be achieved via compartmentalization and tagging with molecular barcodes. Compartmentalizing in the context of this disclosure refers to the act of partitioning a plurality of cSPNAs into a multitude of discrete compartments such that each compartment is allocated with a sub-haploid quantity of nucleic acids. In cases of "physical" compartmentalization, a plurality of cSPNAs can be partitioned into discrete physical spaces (i.e. compartments) that are barred from intermixing with other compartments. Such a physical compartment might be the well of a microtiter plate (e.g. as in CPT-Seq[21,22]), or a microfluidic droplet (e.g. as in 10× Genomics[23]). In cases of "virtual" compartmentalization, a plurality of cSPNAs are tagged via transposition by transposases affixed to a solid substrate, such that the uniquely barcoded transposases affixed to the solid substrate represents its own "virtual" compartment and is not physically barred from intermixing with other virtual compartments (e.g. as in CPT-seqV2[24]).

Tagging: Tagging in the context of this disclosure refers to physically integrating unique molecular identifiers (i.e. molecular barcodes, defined below) as part of (or in amplicons of) the cSPNAs. As described herein, molecular barcodes can be integrated into cSPNAs using transposases to integrate a uniquely barcoded oligonucleotide into the cSPNAs, or, via techniques such as primer extension polymerization (PEP), where a polymerase and a primer comprising a molecular barcode anneals to and extends along the cSPNAs, thereby creating amplicons of the cSPNAs that are contiguous with the barcoded primer nucleic acids. Also described is an alternate form of tagging involving the ligation of an oligonucleotide comprising a molecular barcode to a terminal end(s) of cSPNAs.

Molecular Barcode: A molecular barcode in the context of this disclosure refers to a uniquely identifiable nucleic acid sequence that uniquely informs the context for which the molecular barcode was introduced. For example, when a molecular barcode is integrated into cSPNAs and subsequently sequenced, the molecular barcode manifested in the sequencing readout informs which cSPNAs the sequence readout originated from.

Nucleic acid template: In the context of this disclosure, a nucleic acid template (or "template" for short) refers to the nucleic acid molecule(s) that are read by a sequencing instrument. The process of generating nucleic acid templates often involves nucleic acid fragmentation to a molecular length recommended for a specific sequencing instrument. For example, current Illumina short-read sequencing mandates a nucleic acid lengths of approximately 500 bp.

BRIEF DESCRIPTION OF THE DRAWINGS

FIG. 5 Effects of PL templates on variant sensitivity. PL templates from 3C and HiC were prepared from GM12878 cells and sequenced to 30× depth. As an external control, a non-PL template wherein nucleic acids are isolated and fragmented to 500 bp, was prepared as a conventional short-read template that is then sequenced (also referred to as whole-genome sequencing (WGS) data)). All sequence data were aligned to hg19 human reference genome and genomic variants (SNVs) were identified using in-house pipeline and GATK[26]. In (i), we plot $V_s$ as a function of distance from the nearest RE digestion site. For the WGS external control, we conducted the same analysis, but because WGS template preparation does not involve digestion via REs, we used the 'GATC' motif for digestion sites because that is the motif recognized by the RE that were used to prepare both PL templates. We plotted $V_s$ at every base up to +/−1 Kb from a digestion site. In (ii), we plot the $V_s$ determined from each sequencing data set, revealing quantitatively similar $V_s$ between 3C and WGS (~95%), but limited $V_s$ from HiC (~60%). HiC sequence data were downloaded from Rao et al[28]. WGS data were downloaded from DePristo et al[29]. Arima Genomics generated 3C templates and sequencing data.

FIG. 6 Limited Haplotype phasing capability in sequence data from PL templates. To prepare templates for sequencing, 3C comprises of fragmenting LPs and preparing all fragments as a template for sequencing. HiC comprises fragmenting MLPs and the MLP fragments comprising LJ are enriched and prepared as a template for sequencing. 2 replicates of 3C templates and 1 replicate HiC template were generated from GM12878 cells and sequenced to 30× depth. 3C and HiC sequence data were aligned to the hg19 human reference genome and genomic variants (SNVs) were identified using in-house pipeline and GATK[26] and haplotypes were assembled using in-house pipeline and HapCUT2[30]. In (i), we plot the span of the largest haplotype block ($H_c$) of a target region (a given chromosome in this case). In (ii) and (iii), we plot whole-genome $H_r$ and whole-genome $H_a$, respectively. 'Whole-genome' indicates that $H_a$ and $H_r$ statistics were calculated based on data from the entire genome as the target region. Arima Genomics generated 3C and HiC templates and sequencing data.

FIG. 7 Preserving spatial-proximal and molecular contiguity in PL templates can improve haplotype phasing. In (i), we model the probability of a PL template having at least 2 genomic variants (e.g. SNVs)—a requirement to inform haplotype phase. For conventional PL templates (e.g. 3C or HiC templates), we assume that if a PL template is 300 bp, and if we assume the genomic variant (SNV) density in human genomes in 1 in 1500 bases (heterozygous SNVs in particular in some human populations are of this density), then the probability of a PL template having at least two genomic variants that inform haplotype phase is ~1.7%—a mathematically estimate by assuming genomic variants are uniformly distributed in the template. Therefore, conventional PL templates (e.g. 3C or HiC templates) that only preserve spatial-proximal contiguity via LPs have low probability of informing haplotype phase, whereas longer PL templates that preserve both spatial-proximal and molecular contiguity have higher probability to manifest at least two genomic variants to critically inform haplotype phase. In (ii), we analyzed HiC sequencing data from GM12878 cells by aligning the data to the hg19 human reference genome and then simulated longer template lengths by artificially extending the read lengths beyond the original (300 bp, 150 bp paired-end) length up to 2 Kb. Then, we assumed a known set of genomic variants (SNVs) and used in-house pipelines and HapCUT2[30] to haplotype phase the genomic variants and calculate $H_r$ (y-axis) at various sequencing depths (x-axis). Clearly, preserving both spatial-proximal and molecular contiguity via longer PL templates generates higher resolution of haplotype phase. Arima Genomics generated the HiC templates and sequencing data.

FIG. 8 Mathematical demonstration of improved $H_a$ due to preservation of both spatial-proximal and molecular contiguity in PL templates. This hypothetical 3 Kb region of chr6 contains 5 genomic variants (SNVs) (last 3 digits of SNV positions shown in boxes beneath chr6 track) and two haplotypes are possible, denoted as 'H1' or 'H2'. (i) From HiC sequence data, where only spatial-proximal contiguity is preserved in the templates via MLPs, phasing between variants 298 and 308 is incorrectly predicted due to few (say n=3) HiC read-outs informing haplotypes between these genomic variants. That is, the limited HiC sequence read evidence suggests that the incorrect haplotype (GAT/AGA) is 24 times more likely than the correct haplotype (GAA/AGT). In 3C sequence data, $V_s$ is improved to define more genomic variants and thus variants 811 and 975 are introduced. However, because 3C templates also preserve only spatial-proximal contiguity via LPs and poorly preserve molecular contiguity, there is no improvement in creating new haplotype phase information and thus even when 811 and 975 are identified, they cannot be phased, and haplotype phasing remains erroneous. Thus while $V_s$ is improved, $H_a$ and $H_r$ remain limited in 3C sequence data. (ii) By preserving of both spatial-proximal and molecular contiguity (e.g. via longer PL templates and other means as discussed below in CPSP-Prep), new haplotype phase information is introduced and consequently more variants can be phased, and with higher accuracy. In this example, preserving of both spatial-proximal and molecular contiguity improves $H_r$ by enabling haplotype phasing of variants 811 and 975, and in addition improves $H_a$ as the new haplotype information outweighs the previous incorrect prediction >8-fold (0.0003 vs. 0.0025). Overall, preserving both spatial-proximal and molecular contiguity improves overall haplotype performance—the fundamental concept behind CPSP-Prep and CPSP-Seq.

FIG. 10 Limited preservation of spatial-proximal contiguity in nucleic acid templates (i) Sequence data from conventional PL templates can categorize cSPNAs into groups that inform spatial-proximal contiguity. Specifically, cSPNAs can originate from different chromosomes (in "trans"), or from the same chromosome (in "cis"). Within the cis SPNAs, they can be further classified into cSPNAs that are greater than 15 Kb in linear sequence distance ("long-cis"), or cSPNAs within 15 Kb ("short-cis"). While all groupings of cSPNAs are informative for some applications (e.g. genomic variants (SNV or structural rearrangement) detection), the long-cis cSPNAs are most informative for contiguity applications (e.g. haplotype phasing or de novo assembly of targeted region). To determine the extent to which PL templates derived from LPs preserve spatial-proximal contiguity, we prepared LPs using published methods[31-34] involving restriction digestion with HindIII, followed by fragmentation, preparation as a template and short-read sequencing. As a proxy for the preservation of spatial-proximal contiguity, we asked what fraction of readouts are long-cis, and from published PL template methods, only ~2% of templates are long-cis, revealing a deficiency in spatial-proximal contiguity using published PL workflows. (ii) A source of nucleic acids (i.e. GM12878 cells) was subjected to digestion using HindIII. The nSPNAs after digestion were analyzed on a TapeStation to measure average nucleic acid molecular length (in Kb, x-axis).

FIG. 14 Longer molecular lengths in LPs prepared using optimized 3C methods. A source of nucleic acids (i.e. GM12878 cells) was subjected to digestion using HindIII, MboI, or NlaIII as well as optimized chromatin solubility biochemistry (40 min), as discussed in FIG. 13. The LPs (cSPNAs) generated after ligation were analyzed on a TapeStation to measure average nucleic acid molecular length (in Kb, x-axis), and LPs from each RE are indicated.

FIG. 19 Innovations towards optimizing tagging yield obtained from tagging LPs from PL methods in CPSP-Prep via RE and tagging duration optimizations. In order to improve PEP-based tagging yield, we hypothesized that LPs prepared using different REs could possess properties that improve the efficiency of the compartmentalization or tagging reaction (i.e. such as LPs with longer molecular length). Therefore, in (i) we prepared LPs using either DpnII or NlaIII and subjected 1 ng of each to PEP-based tagging via methods reported by 10× Genomics and using 10× Genomics instrument and consumables. As a control, we also subjected 1 ng of HMW gDNA to the same procedure. While LPs prepared via DpnII only reached ~2.6% relative yield, LPs prepared via NlaIII increased tagging yield >10-fold, reaching ~29% yield relative to HMW gDNA control, but still significantly below the desired result. These data indicate how optimizing the RE used the LP generation can have significant impact of compartmentalizing and/or tagging. In (ii) we hypothesized that extending the tagging duration may allow for the PEP-based tagging reaction to overcome inefficiencies and reach the desired tagging yield. To test this, we prepared LPs using NlaIII and subjected 1 ng of LPs to either the standard 3 hr or extended 6 hr tagging duration and quantified the PEP-based tagging yield. As a control for expected yield after a standard 3 hr tagging reaction, we subjected 1 ng of HMW gDNA to 3 hr tagging and plotted the tagging yield from LPs relative to the expected yield from 3 hr HMW gDNA tagging. These data indicate that extending the tagging yield beyond the recommended 3 hr to 6 hr increases the LP tagging yield to an amount comparable to that of the HMW gDNA control, a vital optimization to obtain high quality and complex nucleic acid templates from these aspects of CPSP-Prep.

FIG. 15iii), then (i) SSPC products are first compartmentalized. In one aspect of the method, (ii) spatial-proximal contiguity is preserved in the subsequent CPSP-Prep templates by first ligating oligonucleotides comprising compartment-specific molecular barcodes. Then, (iii) molecular contiguity is preserved in the CPSP-Prep templates derived from the SSPC products by preparing HML templates, which are subsequently sequenced via long-read sequencing instruments (e.g. Pacific Bioscience sequencers). The final nucleic acid templates from this method preserve spatial-proximal contiguity in the barcode and preserve molecular contiguity in the length of the nucleic acid template. In another aspect of the method, (iv) spatial-proximal contiguity and molecular contiguity is preserved in the subsequent CPSP-Prep templates by integrating molecular barcodes to the compartmentalized SSPC products (e.g. PEP or transposition). The barcoded fragments are then (v) prepared as a nucleic acid template and sequenced via short-reads. Here, the barcoded CPSP-Prep nucleic acid templates preserve both spatial-proximal and molecular contiguity in a single barcode.

DETAILED DESCRIPTION OF CPSP-PREP AND OBTAINING SEQUENCING DATA THEREFROM (CPSP-SEQ)

Figure 1:
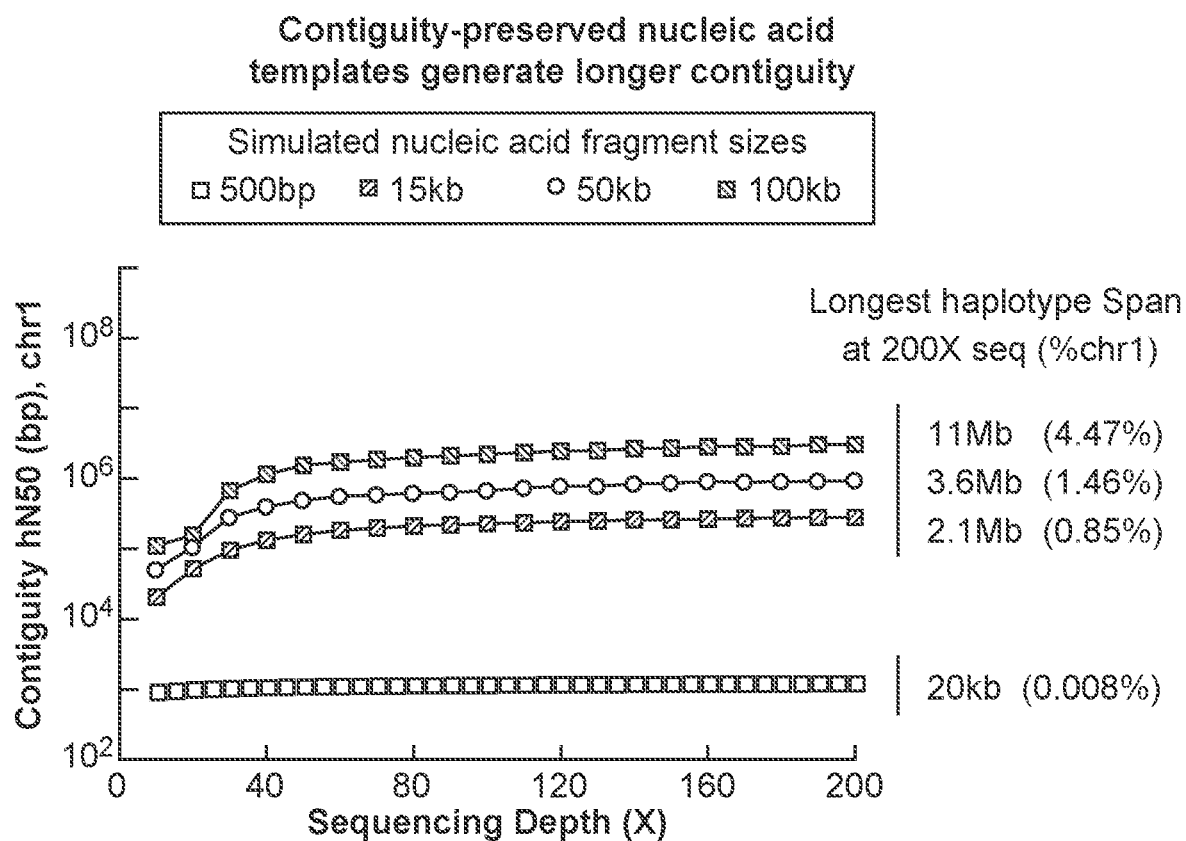
FIG. 1 Contiguity-preserved nucleic acid templates generate longer contiguity. Contiguity is defined as the phenomenon where the sequence of contiguous nucleic acids, as manifested in the nucleic acid template, is determined, and one approach to measure contiguity is the ability to construct haplotypes—longer the span of haplotypes, longer is the contiguity. Of note, a source (cell(s), nuclei, nuclear matrix, etc.) often inherits multiple copies of genetic material (e.g. human somatic cells inherit two copies of genetic material), and haplotypes are the ability to deconvolute copies of genetic material via linking genetic variants. In this figure, we use average haplotype span (hN50) to inform contiguity of nucleic acid sequence. We depict current methods by simulating different nucleic acid fragment lengths manifested in templates prepared for various methods at various sequencing depths (x-axis) and representing contiguity via average haplotype span (y-axis) constructed from single nucleotide variants as manifested in NA12878 genome (human, hg18 reference). These simulations represent short-read (Illumina, 500 bp fragment size) and contiguity-preserved nucleic acid templates (15-100 Kb fragment sizes, contiguity preserved nucleic acid templates are also referred to as synthetic long reads, as generated via PL methods or via other methods such as 10× Genomics[23]). In aligning with real datasets, all simulations allow heterogeneity in nucleic acid fragment sizes, except for the 500 bp simulation modeling Illumina; e.g. for the 15 kb nucleic acid fragment size simulation, we modeled a Gaussian distribution of nucleic acid sizes of mean 15 kb, with std. dev. 10% from mean, mixed uniformly, and represented via 100-bp paired-end sequencing read-outs. Simulation results agree with the literature, showing robustness of our simulation methods[25]. To the right of the plots, we show the span of the longest haplotype span as a measurement of maximum contiguity to estimate the best performance of various nucleic acid fragment sizes within templates at ultra-high 200× sequencing depth to show that contiguity-preserved templates generate longer contiguity.

Despite NGS having emerged as the predominant set of methods for nucleic acid sequence determination, sequencing data from "short-read" methods can only determine the contiguous nucleic acid sequence of a fraction of a chromosome (FIG. 1, 20 Kb longest contiguity). Furthermore, preparation of nucleic acid templates comprising contiguity-preserved nucleic acid molecules that are subsequently sequenced, results in generation of sequencing data that preserves longer contiguity (FIG. 1, 2-11 Mb longest contiguity). In essence, maintaining contiguity during nucleic acid template preparation allows preserving contiguity in sequencing data obtained therefrom. Contiguity-preserved sequencing data enables comprehensive determination of nucleic acid sequence, as manifested in the contiguity-preserved nucleic acid template, by enabling identification of genomic variants, determination of contiguity information to inform genome assemblies de novo, deconvolution of haplotype phase information, which together are fundamental to understand the role of genetics in living systems.

Figure 2:
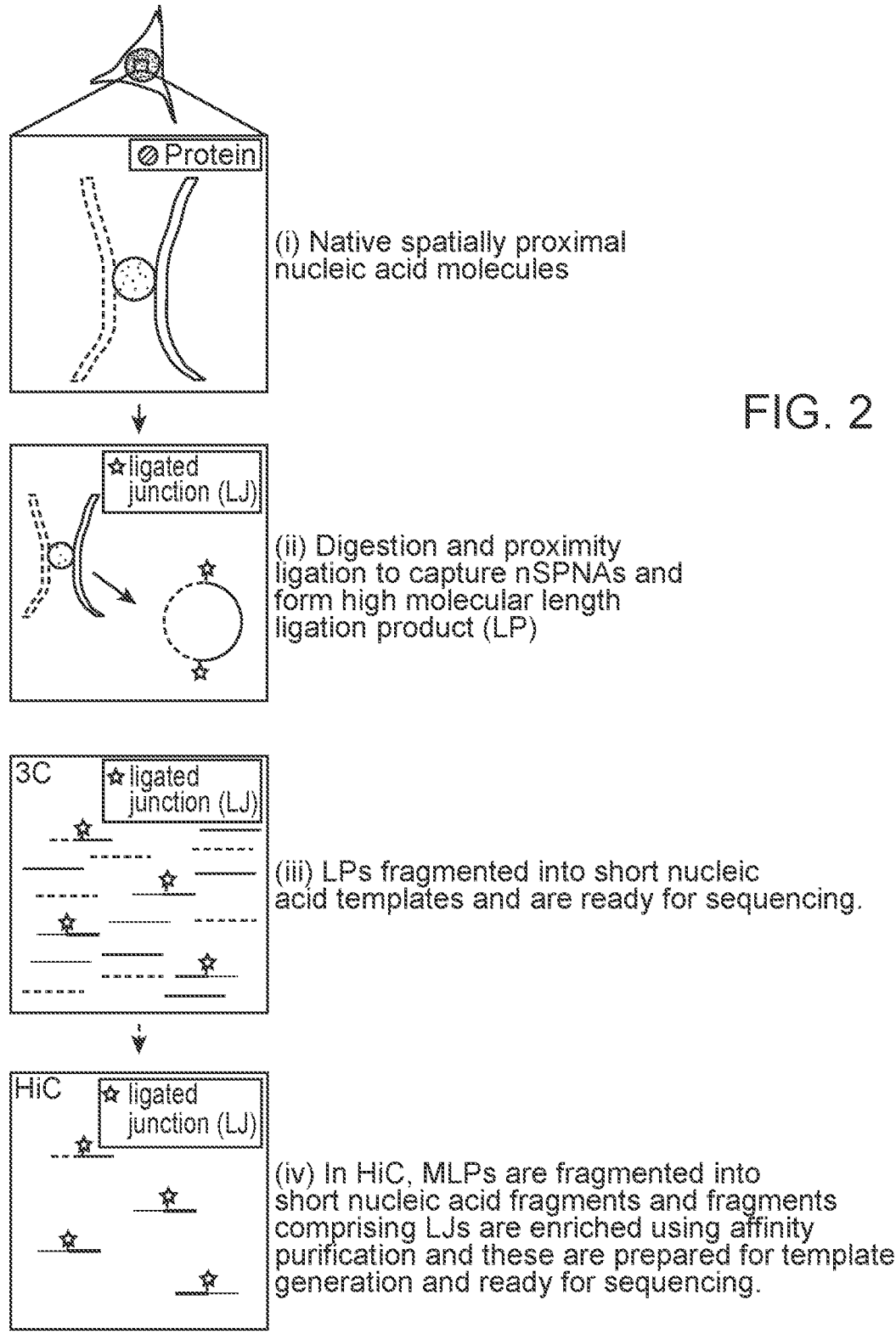
FIG. 2 Schematic of capturing nSPNAs via PL methods. PL methods begin with (i) native spatially proximal nucleic acids (nSPNAs) within a nucleic acids source (e.g. cell(s), nuclei, nuclear matrix (in whole or part), including formalin-fixed paraffin-embedded (FFPE) cell(s) or nuclei or nuclear matrix), followed by (ii) digestion (e.g. via RE) and ligation to generate cSPNAs and form ligation products (LPs). Broadly, PL methods are classified as 3C-based and HiC-based, although there are many specific variations of PL. In 3C[12] (iii), the plurality of LPs are fragmented, prepared as short nucleic acid templates and ready for sequencing. In HiC[17,18] (iv), the digested nucleic acid ends are marked (e.g. biotinylated) and then ligated to create marked ligated products (MLPs, MLPs are a manifestation of LPs), bearing an affinity purification marker at the LJs. After the plurality of MLPs are fragmented, affinity purification is used to enrich for fragments of MLPs comprising LJs and such fragments are prepared as nucleic acid templates and are ready for sequencing—i.e. the fragmented nucleic acids from the MLPs that contain at least an LJ are enriched and prepared as a template and sequenced in HiC, to deplete uMLPs (unligated MLPs that do not usually manifest Us). Regardless of the PL workflow, while generation of LPs (or MLPs) captures and generates cSPNAs, critical information regarding molecular contiguity within an LP (or MLP) is poorly captured as LPs are fragmented into short segments during template preparation process.

In methods involving spatial proximity ligation (referred to as PL methods hereafter)—while generation of LPs informs one form of contiguity (i.e. the spatial-proximal contiguity) via ligating nSPNAs, another key form of contiguity is poorly captured. That is, LPs manifest multiple forms of contiguity—one, by nature of ligating nSPNAs, and second, in their high molecular length (HML), as LPs range in sizes <1 Kb to >60 Kb. While PL methods capture spatial-proximal contiguity, it loses molecular contiguity, as LPs are fragmented, then prepared as nucleic acid templates, and then subjected to sequencing (when plurality of LPs are fragmented into shorter segments to generate nucleic acid templates, the contiguity information of which short nucleic acid fragment originated from which LP is poorly captured or lost), as illustrated in FIG. 2.

In the previous sections, we discussed how contiguity-preserved templates could result in contiguity-preserved sequencing data, which enables comprehensive determination of nucleic acid sequence. To determine nucleic acid sequence, one needs to determine the contiguous sequence of nucleic acids for targeted nucleic acids, including homologous nucleic acids, and identification of genomic variants therein. Specifically, one must (1) determine the contiguous sequence of nucleic acids, ideally the entire targeted region or chromosome of interest, (2) identify nucleic acid sequence variants (e.g. single nucleotide variants (SNVs), structural variants (SVs), or other types of variants) within the targeted region of interest, (3) assign such nucleic acid sequence variants to their respective homologs (i.e. haplotype phasing). In this section, we utilize PL workflows as a means to generate contiguity-preserved templates (via its inherent nature to preserve spatial-proximal contiguity) to demonstrate its ability to determine contiguous nucleic acid sequence and how it can be improved by preserving molecular contiguity in addition to spatial-proximal contiguity to result in CPSP-Seq.

Figure 4:
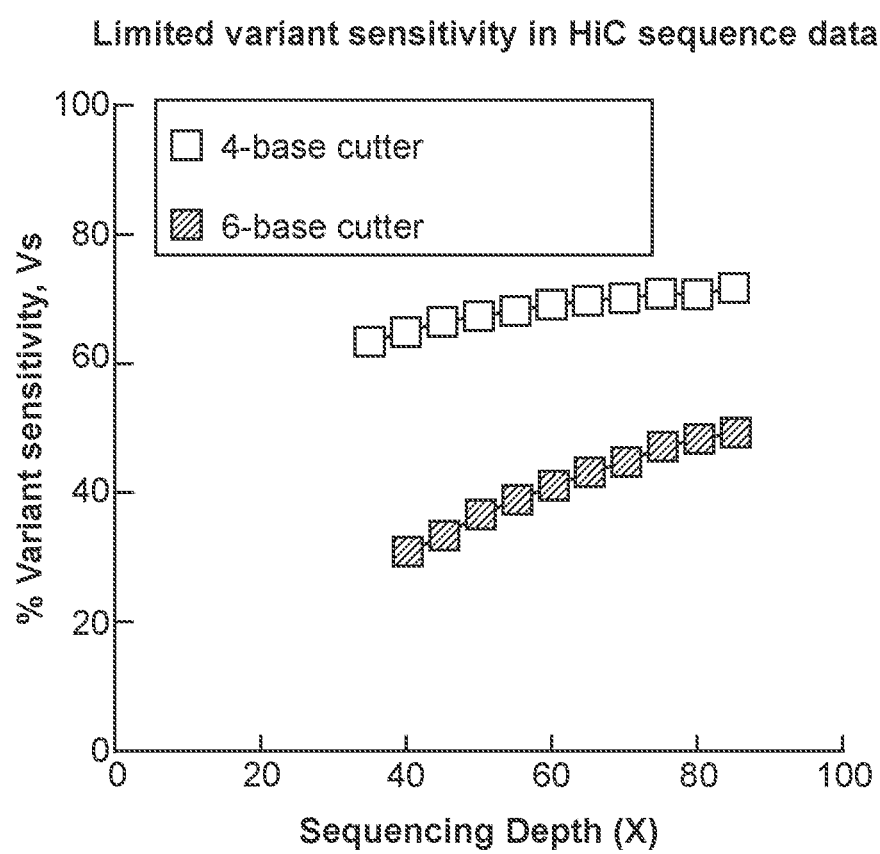
FIG. 4 Limited variant sensitivity in HiC sequence data. In the digestion step of a PL workflow, HiC in this case, digestion is performed by either a 6-cutter or 4-cutter RE to produce HiC templates from GM12878 cells (human lymphoblastoid cell line) and sequenced to up to 90× depth to generate HiC sequencing data. HiC sequencing data was sub-sampled to depths ranging from 35× to 90× depth at 5× increments. HiC sequencing data were aligned to hg19 human reference genome and genomic variants (SNVs) were identified using in-house pipelines and GATK[26]. $V_s$ was determined for each dataset, calculated as the fraction of genomic variants (SNVs) identified in the HiC sequencing data out of the known genomic variants (SNVs) in this sample as identified by an external project named platinum genomes project[27], and plotted on the y-axis for each sequencing depth analyzed. HiC sequence data were obtained from Rao et al[28].

To determine contiguous nucleic acid sequence, PL workflows must create templates (termed 'PL templates') wherein each nucleic acid in the targeted region must be represented and no regions can be intentionally depleted, excluded, or enriched. By analyzing the sequencing data obtained from PL templates, one can ask what fraction of the nucleic acids from the nucleic acids source are represented by sequence data (termed "coverage"), and as a proxy to coverage, one can determine the fraction of the genomic variants (e.g. SNVs), manifested in the targeted region, detected at a given sequencing depth (variant sensitivity; $V_s$). In comparing sequencing data from PL methods of HiC and 3C, we realize that while HiC data generates limited $V_s$, 3C data generates optimal $V_s$ (FIG. 5$i$). More specifically, in HiC, the MLP fragments that contain Us are enriched and prepared as a template and sequenced (FIG. 2$iv$) and because fragmented MLPs are ~500 bp, a genomic variant must be within ~250 bp upstream or downstream of a digestion site in order for it to be represented in HiC sequence data. Conversely, a genomic variant distal to a digestion site is unlikely to be represented in HiC sequence data. The more frequent the digestion site is, higher $V_s$ can be achieved— indeed, analysis of HiC data[28] generated using a 6-base cutting RE for digestion reveals limited $V_s$ which is substantially improved by using a 4-base cutting RE for creating HiC templates and sequencing data (FIG. 4). However, even at ~85× sequencing depth, which is three-times higher than the usual 30× depth, $V_s$ from 4-cutter sequence data does not reach optimal $V_s$ of >95%, indicating that even when sequenced at such high depths, only a fraction of the nucleic acids from the nucleic acids source are represented in HiC sequence data. To further examine the limited $V_s$ from HiC sequence data, we analyzed $V_s$ as a function of the distance that genomic variants are to their nearest digestion site (FIG. 5$i$). $V_s$ drops dramatically for genomic variants distal to the RE digestion sites, with approximately 20% $V_s$ at just 250 bp from the digestion site (FIG. 5$i$). In contrast to HiC templates, 3C templates are prepared by fragmenting LPs, and all the fragmented nucleic acid molecules are prepared as a template for sequencing (FIG. 2$iii$)—that is, in 3C no enrichment towards selecting a sub population of Us is performed (unlike how MLPs with Us are preferentially enriched in HiC). Since there is no enrichment of LP fragments that contain an LJ or any other exclusions or enrichments of nucleic acid molecules during 3C template preparation, all nucleic acids from the nucleic acid source are prepared as a template for sequencing. Indeed, analysis of 3C sequence data at ~30× sequencing depth reveals that $V_s$ is not biased towards restriction digestion sites (FIG. 5$i$) and results in ~95% $V_s$ (FIG. 5$ii$). As an external control to PL methods, we analyzed data[29] from Illumina short-reads in the absence of any contiguity-preservation (referred to as whole-genome sequencing (WGS)). In sum, while HiC prepares nucleic acid templates from the subset of MLP fragments enriched for containing Us leading to limited $V_s$, 3C prepares nucleic acid templates from all nucleic acid molecules from the nucleic acid source leading to optimal $V_s$.

To understand PL methods capability to determine contiguous nucleic acid sequence, we discuss means to measure contiguity. First, contiguity of nucleic acids can be measured by the ability of the sequencing data to assemble target regions de novo. That is, while templates manifest fragmented nucleic acid molecules, contiguity is measured by the capability of sequencing data obtained from such templates to assemble the target regions to their natural form prior to fragmentation. In this context, PL methods (especially HiC) have been used to scaffold and assemble target regions de novo[36-39]. A second means to measure contiguity is via the ability to haplotype phase. That is, the identified genomic variants (e.g. SNVs) need to be assigned to their respective homologous regions resulting in a homologous region that can be defined and differentiated by a haplotype of contiguously linked variants. PL methods have been used for haplotype phasing[40,41] (e.g. PCT/US2014/047243[42] from these inventors). Haplotype phasing of homologous regions can be extended towards deconvoluting species and strains of species from a mixture metagenomics sample[43,44]. While each of these are measurements of contiguity, in the next paragraphs and sections, we take the approach of haplotype phasing to illustrate the capabilities and limitations of PL workflows to achieve long haplotypes and long contiguity, but results, discussions and claims henceforth applies equally to all measurements and types of contiguity.

Haplotype phasing begins with identifying genomic variants, and then linking or assigning them to their respective homologs of the entire target region or chromosome of interest. Haplotype phasing can be measured via the span of the targeted region nucleic acid sequence for which genomic variants can be assigned to their respective homologous chromosome (haplotype completeness; $H_c$); the fraction of genomic variants that can be assigned to a homologous chromosome (haplotype resolution; $H_r$); and the fraction of genomic variants that were correctly assigned to their respective homolog (haplotype accuracy; $H_a$), and optimal contiguity is defined when $H_r$ is >95% and $H_a$ and $H_c$ are >99%. In analyzing PL methods (e.g. 3C, HiC), we realized that while PL methods generate optimal results in $H_c$, its performance towards $H_r$ and $H_a$ is rather limited (FIG. 6). The critical shortcoming to PL methods (e.g. 3C and HiC) is that only one form of contiguity is captured (i.e. spatial-proximal contiguity) in PL templates while a second form of contiguity (i.e. molecular contiguity) is poorly captured as LPs are fragmented prior to template preparation and sequencing, which we hypothesize to lead to limited $H_r$ and $H_a$ (FIG. 6). Specifically, for a PL template to inform haplotype phasing, it must manifest at least two genomic variants, and, if a heterozygous genomic variant that distinguishes homologs occur on average about every 1 in 1500 bases (e.g. in some human genomes), then the probability of a PL template to manifest multiple genomic variants increase with the length of the nucleic acid fragments manifested in the template. We hypothesized that if the molecular contiguity was preserved within LPs and manifested in a high molecular length PL template, then that increased template length is likely to provide more haplotyping phase information in the sequence data. For example, if the LP was fragmented to 2 Kb instead of 500 bp, and prepared as a template for sequencing, then significantly more sequencing read-outs (44%, FIG. 7$i$) would inform haplotype phasing to result in higher $H_r$ (FIG. 7$ii$) and higher $H_a$ (FIG. 8). However, because the conventional and predominant sequencing (short-read sequencing, see definition section) achieves only 500 bp sequencing, preserving molecular contiguity in nucleic acid templates and sequencing longer fragments will require further innovation, as discussed in a section below. Together, the improvements shown in $H_a$ and $H_r$ (FIGS. 7 and 8) are a consequence of preserving both spatial-proximal and molecular forms of contiguity in nucleic acid templates.

As before mentioned, improvements in variant sensitivity and haplotype phasing capabilities of CPSP-Seq will enable CPSP-Seq to improve other means of contiguity such as in assembly of targeted region de novo or strain deconvolution in metagenomic assemblies. In addition, as CPSP-Seq captures nSPNAs via LPs or via SSPC products as discussed below, it informs conformation and topology of target nucleic acids. Interestingly, because structural variations (SVs) such as structural rearrangements (e.g. inversions, translocations) perturb conformation, measuring conformation via CPSP-Seq conversely informs the precise localization of structural rearrangements—overall, by preserving both spatial-proximal and molecular forms of contiguity and conformation, CPSP-Seq will likely have multitude of applications to comprehensively determine nucleic acid sequence and identification of genomic variants.

Technical Description of CPSP-Prep and Obtaining Sequencing Data Therefrom (CPSP-Seq)

The sequence data obtained from PL methods (e.g. 3C and HiC), as manifested in PL templates (FIG. 2), is shown to be inadequate for comprehensive sequence determination, indicated by the limited utility of the data towards identifying genomic variants (e.g. SNVs) and contiguity applications (e.g. haplotype phasing) (FIGS. 4-8). The core workflow of PL workflows comprises (1) capture of nSPNAs by proximity ligation to generate LPs, and (2) fragmenting LPs into short nucleic acid fragments which are prepared as a template for short-read sequencing. Critically, because of this workflow, nucleic acid templates derived from PL workflows capture only one form of contiguity—spatial-proximal contiguity. However, this form of contiguity alone is insufficient for comprehensive sequence determination (FIG. 4-8). To specifically overcome these limitations in sequence data from PL workflows, we developed CPSP-Prep.

CPSP-Prep is a novel method disclosed herein comprising the preparation of a nucleic acid template whereby spatial-proximal contiguity and molecular contiguity are both preserved. The CPSP-Prep workflow comprises distinct methodologies, including (1) capture of nSPNAs to generate cSPNAs using a variety of techniques (e.g. via generation of LPs from PL methods or via generation of SSPC products via SSPC methods, as discussed below), then (2) preserving molecular contiguity within cSPNAs, and finally, (3) preparing a nucleic acid template that preserves both spatial-proximal and molecular contiguity and that can be sequenced via long- or short-reads depending on the specific embodiment of CPSP-Prep. The key high-level difference is that in CPSP-Prep, the cSPNAs are subjected to methods preserving molecular contiguity within the cSPNAs, leading to the preparation of nucleic acid templates that preserve both spatial-proximal and molecular contiguity.

In the sections that follow, we describe each step of the CPSP-Seq workflow. First, we describe methods related to CPSP-Prep, which comprise all experimental methods comprising the preparation of nucleic acids templates, beginning with a description of methods for capturing nSPNAs and followed by descriptions of methods for preserving both spatial-proximal contiguity and molecular contiguity in the nucleic acid templates derived from cSPNAs. We follow this with a description for how to adapt CPSP-Prep towards targeted nucleic acids as this workflow can be applied for whole-genome or targeted nucleic acid sequence determination, as discussed in the final section relating to CPSP-Seq data analysis strategies and applications.

Figure 3:
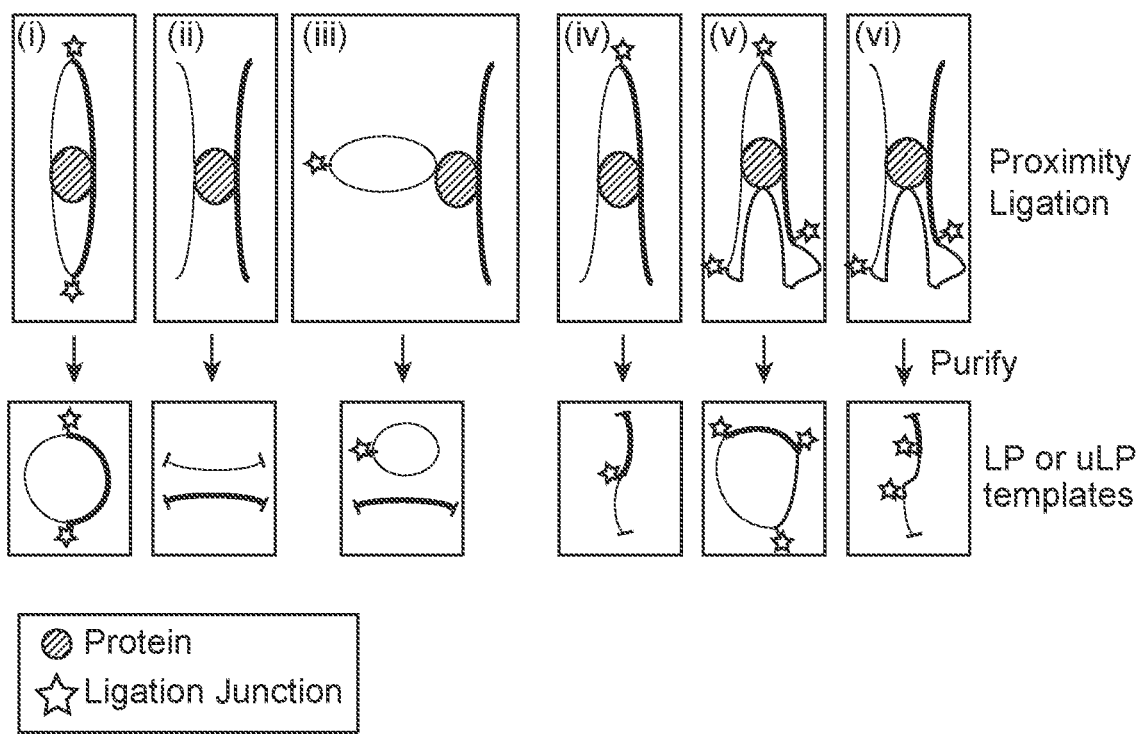
FIG. 3 Myriad of nucleic acid molecule configurations created by PL methods. PL methods begin with nSPNAs within a nucleic acids source (e.g. cell(s), nuclei, nuclear matrix) and post-digestion, nSPNAs are subject to proximity ligation to generate cSNPAs (top row) in the form of ligated and unligated nucleic acid products (bottom row). In (i), ligations occur between two nSPNAs, resulting in a single LP with two LJs. In (ii), neither nSPNA is ligated, resulting in Unligated Products (uLPs) without an LJ. In (iii), an nSPNA ligated to itself, forming a self-ligation product and a uLP. In (iv), only one ligation occurred between two nSPNAs, forming a linearized LP with a single LJ. In (v), three ligations occurred between three nSPNAs, resulting in an LP with 3 Us. In (vi), two ligations occurred between three nSPNAs, resulting in a linearized LP with 2 Us. Notably, other nucleic acid molecule configurations are possible, and this figure aims to illustrate a few common possibilities. Overall, the presence of LJs within LPs (or MLPs in HiC) captures and generates cSPNAs while absence of Us within LPs (or MLPs), as in the case of uLPs, represents poor capturing of cSPNAs.

Capturing nSNPAs Via Proximity Ligation of the Formation of LPs in CPSP-Prep:

As described above, one modality for capturing nSPNAs to generate cSPNAs is via proximity ligation, whereby nSPNAs are captured by ligation (FIG. 2). For this first step of capturing nSPNAs and generating LPs, several types of nucleic acid molecule configurations can be formed, including LPs, MLPs, self-ligated products and uLPs (FIG. 3). Specifically, the most conceptually simple type of LP would be the result of 2 nSPNAs having ligated and formed an LP containing two Us (FIG. 3$i$). However, due to biophysical constraints or molecular biology inefficiencies, not every nSPNAs may be ligated, resulting in uLPs that are nucleic acid molecules lacking Us (FIG. 3$ii$). Another nucleic acid configuration from proximity ligation is a self-ligation, where the two digested ends of a single nSPNA ligate to each other (FIG. 3$iii$). To that end, while LPs are often schematically illustrated as circularized LPs, LPs can also be formed when not all the cSPNAs in an LP have been ligated to another cSPNAs, resulting in the formation of linear LPs (FIG. 3$iv$). Lastly and importantly, LPs can be formed from more than 2 ligations, in which the resulting LPs contain multiple Us between multiple cSPNAs and result in LPs with greater molecular length (FIG. 3$v$-$vi$). In sum, the totality of these types of nucleic acid configurations are generated by PL methods, with a key differentiating factor being that in HiC (or HiC-derived techniques) the LPs and uLPs are marked (e.g. with biotin) to form MLPs (and MuLPs). These MLPs and MuLPs are fragmented and fragments comprising Us are enriched and prepared as a template for sequencing. In other PL workflows, LPs (and uLPs) are unmarked and do not undergo an enrichment procedure but are subjected to similar fragmentation, template preparation and sequencing (FIG. 2$iv$). Each PL method presents certain advantages and disadvantages that necessitate careful considerations and understanding while preparing LP/MLPs for CPSP-Prep (discussed below). Also, beyond the PL method used to create LPs, the composition of an LP, such as the length of the digested nSPNAs, LP length and number of LJs per LP can have considerable impact on CPSP-Prep, as discussed below. An optimal scenario for this aspect of CPSP-Prep (i.e. beginning with nSPNAs captured by PL) is that LPs from a PL method comprise at least 1 LJ—that way, each LP informs spatial-proximal contiguity by capturing nSPNAs to generate cSPNAs. If the output of proximity ligation is mostly uLPs (FIG. 3$ii$) or self-ligated LPs (FIG. 3$iii$), then limited spatial-proximal contiguity is informed. That is, PL methods with lower ligation efficiency are likely to generate LPs with fewer Us to poorly preserve spatial-proximal contiguity. In contrast, PL methods with high ligation efficiency will generate LPs with more LJs to preserve spatial-proximal contiguity and in addition, higher ligation efficiency can also enable generation of longer LPs wherein the molecular contiguity can be preserved subsequently via methods discussed in next sections. Thus, a critical point to this aspect of CPSP-Prep is to obtain optimal ligation efficiency to preserve optimal amounts of spatial-proximal contiguity and to generate longer LPs for future preservation of molecular contiguity. To achieve optimal ligation efficiency, we pursued stepwise innovation: (1) we compared and contrasted current PL methods of HiC and 3C to understand their properties towards ligation efficiency; (2) given a PL method, we innovated methods to generate optimal ligation efficiency.

Due to a variety of experimental parameters, various PL methods to generate LPs are expected to have varying degrees of ligation efficiency. For example, 3C involves proximity ligation between digested cohesive ends[12] (i.e.

Figure 9:
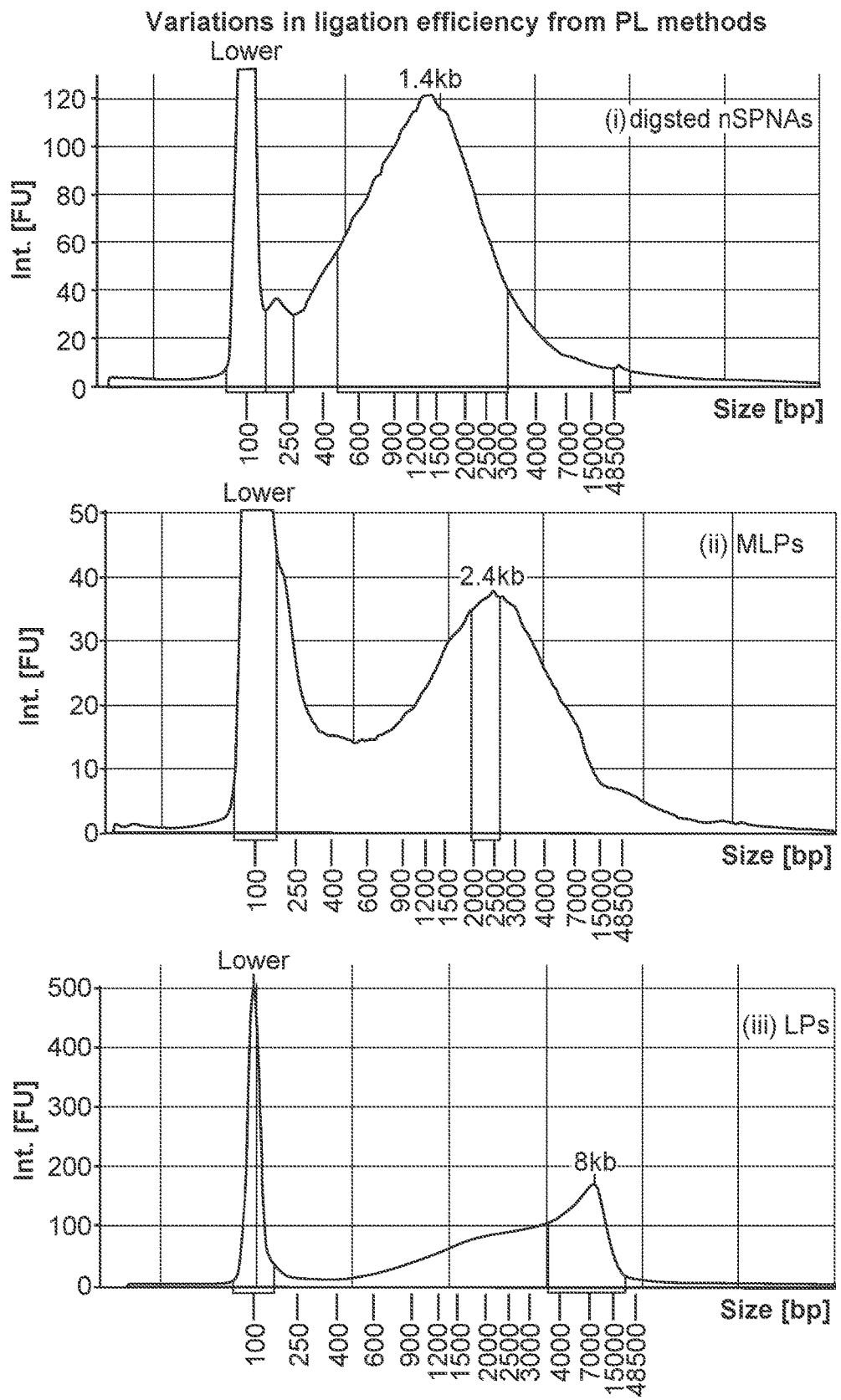
FIG. 9 Variations in ligation efficiency from PL methods. Ligation efficiency of digested nSPNAs varies depending on the PL method and choice of RE. A source of nucleic acids (i.e. GM12878 cells) was subjected to 3C or HiC using DpnII for digestion. The nSPNAs after digestion, and cSPNAs after ligation, were analyzed on a TapeStation to measure average nucleic acid molecular length (in Kb, x-axis). In (i) digestion with DpnII and the digested nSPNAs were analyzed. In (ii) digestion with DpnII and subjected to HiC, and the MLPs (cSPNAs) were analyzed. In (iii) digestion with DpnII and subjected to 3C, and the LPs (cSPNAs) were analyzed. The results indicate that 3C-based LPs are longer than HiC-based MLPs, which suggest 3C methods might manifest higher ligation efficiencies, enable more preservation of contiguity within LPs, and thus are more favorable towards CPSP-Prep.
Figure 11:
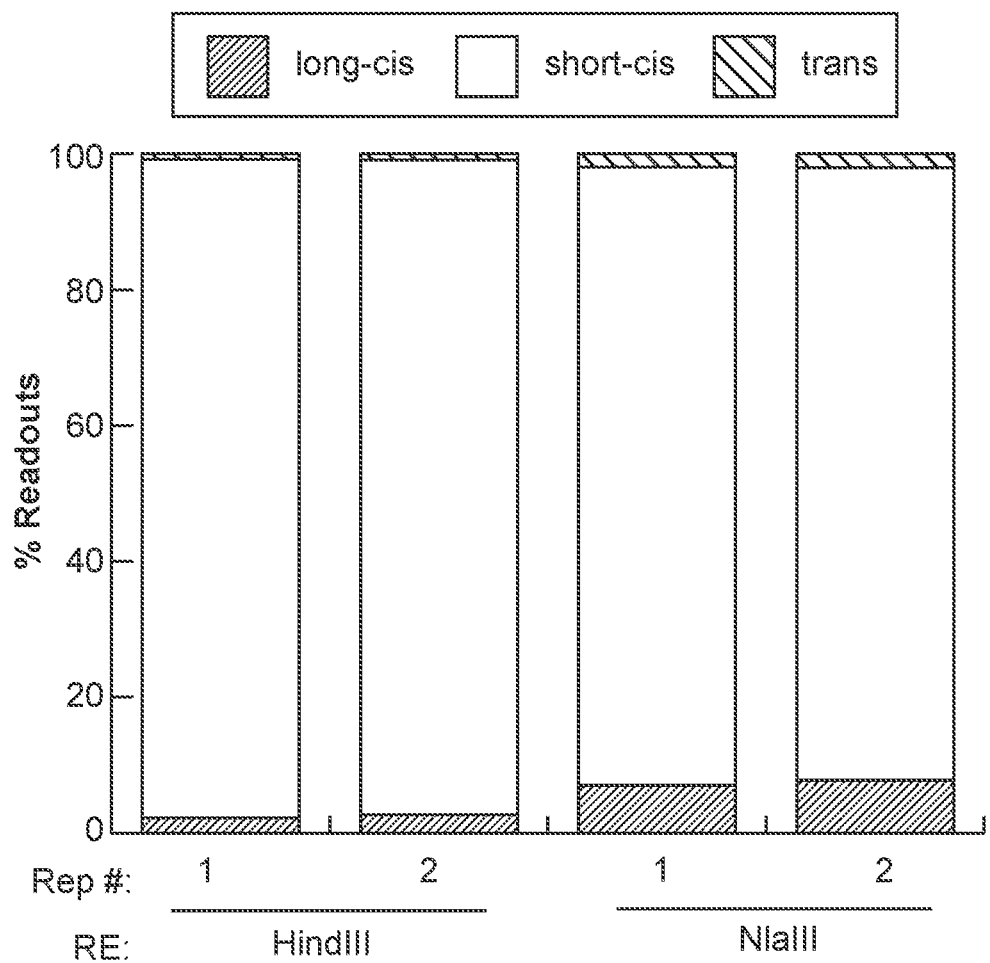
FIG. 11 Improved preservation of spatial-proximal contiguity in PL nucleic acid templates via innovations in RE optimization. In order to increase the fraction of readouts informing spatial-proximal contiguity, we posited that digesting the nSPNAs with a more frequently cutting RE may increase the frequency of LJs within an LP and in turn result in a higher fraction of PL templates comprising an LJ and informing spatial-proximal contiguity. We prepared LPs using published methods[31-34] involving restriction digestion with 6-cutter HindIII (same data as shared in FIG. 10), or, using the 4-cutter RE NlaIII, followed by fragmentation, preparation as a template and short-read sequencing. As a proxy for the preservation of spatial-proximal contiguity, we asked what fraction of readouts are long-cis, and from published PL template methods using HindIII is only ~2% long-cis, while ~7% of PL templates from NlaIII are long-cis. This indicates that the spatial-proximal contiguity signal can be improved by choice of RE.

"sticky ends") whereas HiC involves proximity ligation between blunt ends[17]. These two forms of ligation are known to have vastly different efficiencies and in particular, cohesive end ligation in 3C is hypothesized to be 10- to 100-fold more efficient. To validate this hypothesis, we analyzed nucleic acid fragment lengths from digested nSP-NAs, and again after proximity ligation (FIG. 9). We observed that the digested nSPNAs are 1.4 Kb in length which resulted in 2.4 Kb MLPs from HiC (FIG. 9i,ii). That is, while MLPs preserve spatial-proximal contiguity by manifesting LJs, the 2.4 Kb size of MLPs seem relatively small in molecular length and thus cannot enable significant preservation of molecular contiguity. In contrast, LPs generated via 3C-based PL approach generated LPs of ~10 Kb in molecular length (a 4-fold increase in comparison to MLPs), suggesting that there have likely been more ligations between nSPNAs in 3C, and that 3C-derived LPs likely have more Us per LP and overall longer molecular length of LPs (FIG. 9iii). Because of the higher ligation efficiency inherently enabled by the cohesive end ligation in the 3C method, the 3C method appears to have some capability to preserve spatial-proximal contiguity and to generate longer LPs for subsequent preservation of molecular contiguity. In addition, 3C-based approaches (FIG. 4) have the aforementioned improved $V_s$.

Figure 12:
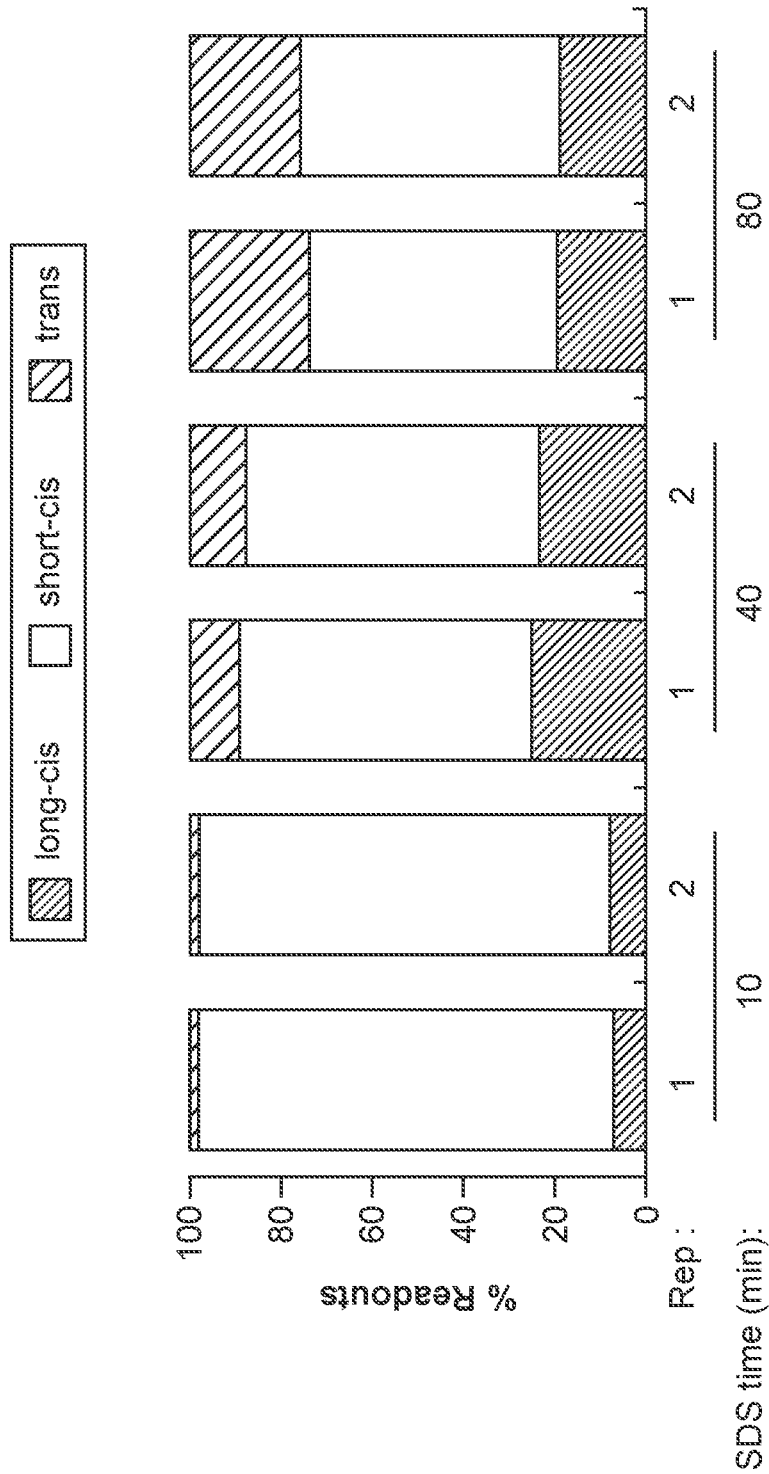
FIG. 12 Optimal preservation of spatial-proximal contiguity in PL nucleic acid templates via innovations in chromatin solubility optimizations. To further increase the fraction of long-cis readouts informing spatial-proximal contiguity, we posited that optimizing the solubility of chromatin via sodium dodecyl sulfate (SDS) prior to digestion and ligation might increase the experimental efficiency leading to a higher fraction of PL templates comprising an LJ and informing spatial-proximal contiguity. We prepared LPs using the previously presented 4-cutter RE NlaIII, but solubilized the chromatin prior to digestion using the published time of 10 minutes of SDS treatment (REF), or extended treatments of 40 or 80 minutes. Once LPs were generated, we continued with fragmentation, preparation as a template and short-read sequencing. As a proxy for the preservation of spatial-proximal contiguity, we asked what fraction of readouts are long-cis, and from published SDS treatment time of 10 min only ~7% of templates are long-cis, while 40 minutes of SDS treatment dramatically increased this fraction to ~24%, yet even longer SDS treatment times caused a relative reduction of long-cis signal to ~19%. Not only does this indicate that the spatial-proximal contiguity signal can be dramatically improved by chromatin solubility optimization, it also demonstrates that it must be carefully optimized as too much SDS treatment reduces long-cis signal. Collectively, we have improved the long-cis signal >10-fold from ~2% using published PL methods to ~24% using optimized RE and chromatin solubility.
Figure 13:
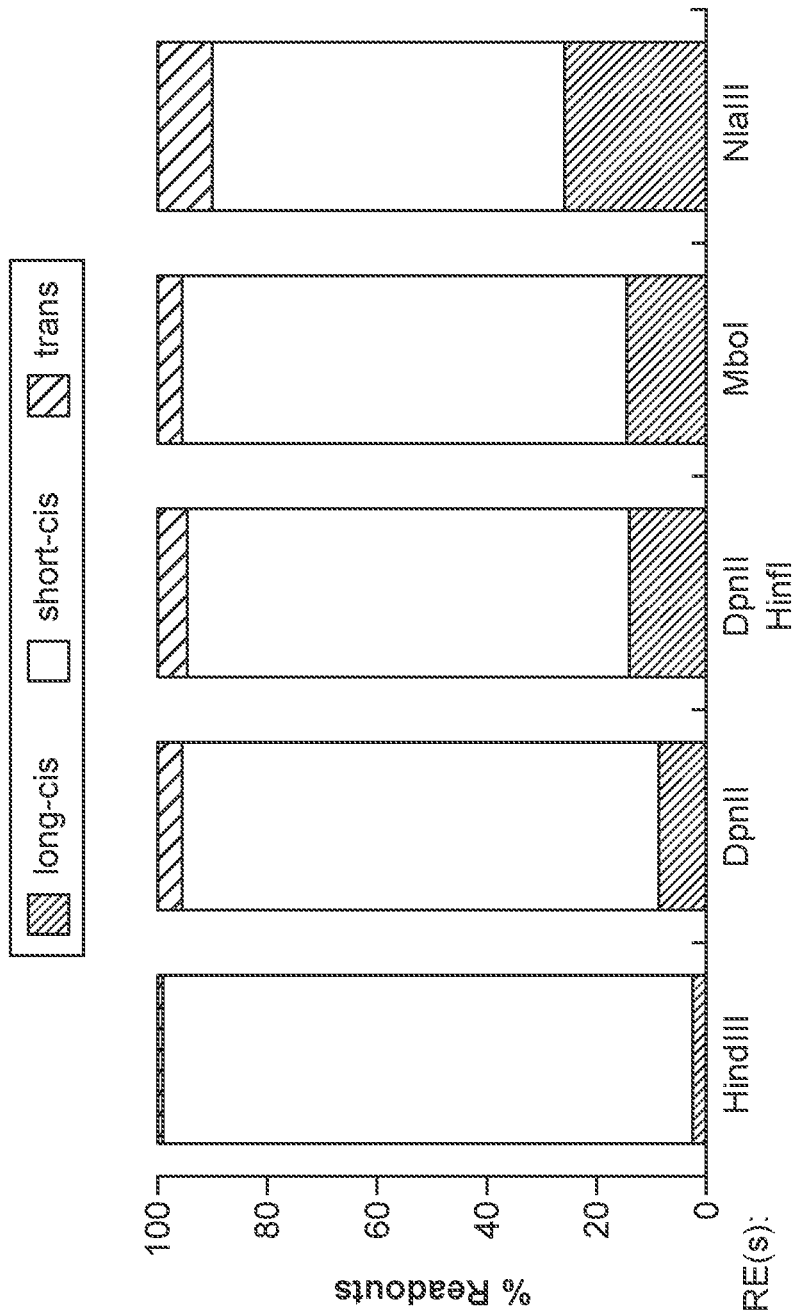
FIG. 13 Preservation of spatial-proximal contiguity in PL nucleic acid templates is optimally preserved with NlaIII. In order to comprehensively examine how choice of RE impacts the preservation of spatial-proximal contiguity in nucleic acid templates in the context of optimized chromatin solubility, we prepared LPs using our optimized SDS treatment time (40 min) using a variety of RE (HindIII, MboI, DpnII) or novel RE combinations (DpnII+HinfI), and then proceeded with fragmentation, preparation as a template and short-read sequencing. As a proxy for the preservation of spatial-proximal contiguity, we asked what fraction of readouts are long-cis. While our previously optimized NlaIII preparation method obtained high long-cis signal (~26%), all other LP preparation methods achieved substantially less, ranging from ~2% for HindIII to ~14% for MboI. Importantly, the frequency at which a RE(s) or digest chromatin is not necessarily correlated with long-cis signal, as using multiple 4-cutter REs (DpnII+HinfI) did not result in the optimal long-cis signal. These data indicate that LP generation using NlaIII uniquely prepares optimal preservation of contiguity in nucleic acid templates.

While 3C-based methods seemingly manifest higher ligation efficiency than HiC-based methods (FIG. 9), and thus generate longer LPs to better enable preservation of molecular contiguity, the LPs generated from conventional 3C-based approaches do not necessarily generate optimal ligation efficiency for subsequent preservation of spatial-proximal contiguity. Therefore, 3C-based LPs generated using published methods do not enable the optimal preservation of both contiguities, making them unsuitable for CPSP-Prep. To illustrate this, we prepared LPs using 3C methods[12,32-34]. Specifically, we generated digested nSP-NAs with HindIII, ligated the digested ends to form LPs, then fragmented LPs to prepare nucleic acid templates and sequenced via short reads. We observed that only ~2% of the readouts are long-cis, a metric proxy to informing spatial-proximal contiguity, indicating that only a very small fraction of templates from known 3C methods preserve spatial-proximal contiguity (FIG. 10i). To understand why such a low fraction of the readouts inform spatial-proximal contiguity, we analyzed the nucleic acid fragment lengths of the digested nSPNAs after HindIII digestion but pre-ligation, and observed that digested nSPNAs are ~21 Kb (FIG. 10ii), and because short-read sequencing sequences ~500 bp nucleic acid templates, the 21 Kb pre-ligated digested nSP-NAs can only result in ~2% long-cis. To improve the long-cis fraction, we hypothesized that digesting the nSP-NAs with more frequently cutting REs could increase the frequency of LJs within LPs, and in turn increase the fraction of nucleic acid templates comprising an LJ and preserving spatial-proximal contiguity. To validate this hypothesis, we utilized a RE that recognizes a 4-base nucleic acid motif (NlaIII), which digests nucleic acids 16-fold more frequently than HindIII. We prepared 3C templates using NlaIII and sequenced via short reads and observed 3-fold higher long-cis (7%) readouts than when preparing LPs using HindIII (FIG. 11), supporting our hypothesis. However, even a ~7% long-cis suggests only a minor fraction of templates manifest LJs to preserve spatial-proximal contiguity. To further improve digestion and ligation efficiency, we posited that optimized chromatin solubility and decondensation would enable more efficient RE digestion and ligation, in turn leading to a greater abundance and frequency of Us in LPs and subsequently more Us in the nucleic acid templates. Indeed, by extending the chromatin solubilization and decondensation reaction from 10 minutes up to 40 minutes, we observed an additional >3-fold (24%) increase in long-cis (i.e. a 10-fold increase in long-cis compared to the original HindIII based LPs) (FIG. 12). Importantly, increasing chromatin solubilization and decondensation time further to 80 minutes led to slightly reduced long-cis, thus 40 minutes seems to be the optimal time that resulted in optimal long-cis. Overall, by innovatively combining careful selection of RE and by improving experimental efficiencies via optimal chromatin solubilization, digestion, and ligation, we show that optimal preservation of ligation efficiency and thus the spatial-proximal contiguity in nucleic acid templates is feasible (FIG. 13).

Critically, these rigorous optimizations enable CPSP-Prep by focusing on experimental parameters that distinctively benefit CPSP-Prep in ways that have not been examined. In sum, we have observed that following PL methods, such as 3C[31-34] or HiC[28], generates limited ligation efficiency and thus limits the potential contiguity that can be preserved in the nucleic acid templates derived from LPs, but that our innovatively optimized PL version (discussed as improvements to 3C) is uniquely optimized to better preserve spatial-proximal contiguity and to generate longer LPs. Specifically, to make 3C-based LPs amenable to CPSP-Prep, we optimized experimental parameters to improve long-cis to improve spatial-proximal contiguity. Further, our optimizations also enable generation of longer LPs (FIG. 14) that in turn can enable greater preservation of molecular contiguity via methods discussed in next sections. In sum, our methods enable significant preservation of spatial-proximal contiguity and generate longer LPs to enable the preservation of molecular contiguity in nucleic acid templates, satisfying the central goal of CPSP-Prep—for example, the data presented herein indicate that 3C-based LPs generated via NlaIII and optimal chromatin solubility are favorable for optimal preservation of spatial-proximal contiguity as these templates optimize long-cis (~24%), while 3C-based LPs generated via MboI and optimal chromatin solubility are favorable for enabling the preservation of molecular contiguity due to the long (>60 Kb) LPs. The careful optimizations of both long-cis and LP length (FIGS. 10-14) described herein are critical aspects of CPSP-Prep. For example, the optimized PL version using NlaIII is preferred over the PL version using MboI because it greatly optimizes long-cis (~26%) and thus preservation of spatial-proximal contiguity in nucleic acid templates, and has been demonstrated to result in complete chromosome-span haplotypes, a metric for optimal contiguity (FIG. 6i). Whether the reduced long-cis fraction (~14%) in nucleic acid templates derived from MboI-based LPs would be able to achieve such complete contiguity in CPSP-Prep, has not yet been demonstrated.

Figure 15:
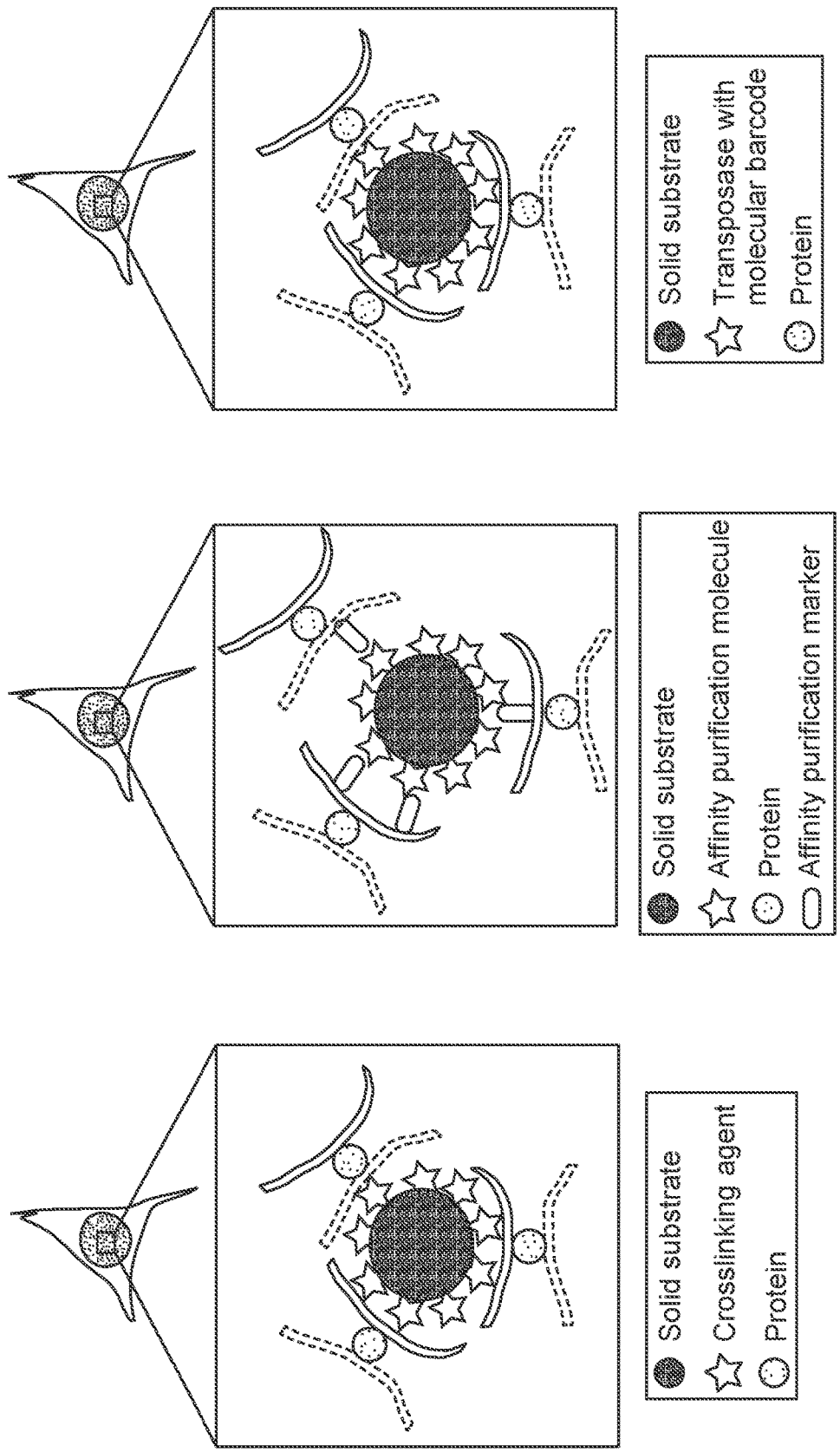
FIG. 15 Schematic of capturing nSPNAs via SSPC methods. SSPC methods comprise introducing an exogenous solid substrate functionalized with surface molecule(s) that captures nSPNAs by binding them. In all cases, the solid substrate is introduced into a source of nucleic acids (cell(s), nuclei, nuclear matrix (in whole or part), including formalin-fixed paraffin-embedded (FFPE) cell(s) or nuclei or nuclear matrix), and in (i) the solid substrate is functionalized with a nucleic acid crosslinking agent such that the surface of the solid substrate becomes chemically bound to the nSPNAs for which it physically contacts. In (ii) the nucleic acids of the nucleic acid source are first labeled with an affinity purification marker and then a solid substrate functionalized with an affinity purification molecule is introduced such that the surface of the solid substrate becomes chemically bound to the labeled nSPNAs for which it comes it physical contacts. In (iii) the solid substrate is functionalized with transposase bearing barcoded oligonucleotides, such that each solid substrate has its own set of uniquely barcoded oligonucleotides, and such that when the surface of the solid substrate comes in physical contact with nSPNAs, the barcoded oligonucleotides are integrated into nSPNAs.

Capturing nSNPAs Via SSPC and the Formation of SSPC Products in CPSP-Prep:

While generation of LPs is one approach to capture nSPNAs to generate cSPNAs, SSPC methods are an alternative approach. SSPC methods inform spatial-proximal contiguity by introducing an exogenous solid substrate that captures nSPNAs by means of the solid substrate binding, in one form or another, to a set of nSPNAs, to generate cSPNAs (FIG. 15). Specifically, SSPC methods capture nSPNAs resulting in SSPC products, but the modality of capturing nSPNAs depends on the design of solid substrate—i.e., capturing of nSPNAs is determined by the size and shape of the solid substrate and its surface molecules and properties. In one aspect of SSPC, a solid substrate (e.g.

bead) is functionalized (e.g. coated) with a nucleic acid crosslinking agent (e.g. psoralen), and nSPNAs are captured via chemical binding between nSPNAs and the surface of the solid substrate (FIG. 15i). In this aspect of SSPC, each individual solid substrate informs spatial-proximal contiguity by binding nSPNAs, and spatial-proximal contiguity is preserved in a molecular barcode introduced during nucleic acid template preparation, as described in a below section. In another aspect of SSPC, the nucleic acids within a nucleic acid source are first labeled with an affinity purification marker (e.g. biotin), and a solid substrate functionalized with a molecule capable of binding the affinity purification marker (e.g. streptavidin) is introduced and binds the labeled nSPNAs (FIG. 15ii). Similar to the aforementioned crosslinking-based SSPC method, spatial-proximal contiguity in this current method is also preserved in a molecular barcode introduced during nucleic acid template preparation, as described in a below section. In another aspect of SSPC, a solid substrate is functionalized with transposases carrying oligonucleotides comprising a unique molecular barcode. Here, each solid substrate is functionalized with transposases loaded with a solid substrate-specific molecular barcode. In this method, the solid substrate comes into physical contact with nSPNAs and the surface transposases integrate uniquely barcoded oligonucleotides into the nSPNAs (FIG. 15iii). Here, spatial-proximal contiguity is informed by the molecular barcode introduced by the transposases. Of note, this aspect of SSPC is similar to the concept of "virtual" compartmentalization (see Definitions section), but different in the application of the concept. Specifically, virtual compartmentalization is a technique that has been applied to preserve molecular contiguity[24], whereas the SSPC approach utilizes transposases for capturing and preserving spatial-proximal contiguity. Regardless of the SSPC method to capture nSPNAs to generate cSPNAs and form SSPC products, CPSP-Prep uniquely introduces a second step to preserve molecular contiguity within the cSPNAs, ultimately leading to the preparation of a nucleic acid template where both spatial-proximal and molecular contiguity are preserved. The sections below assume that nSPNAs have already been captured to form cSPNAs via PL or SSPC methods (as indicated), and it discusses the means by which both forms of contiguity can be preserved from cSPNAs and subsequently in CPSP-Prep nucleic acid templates.

Figure 16:
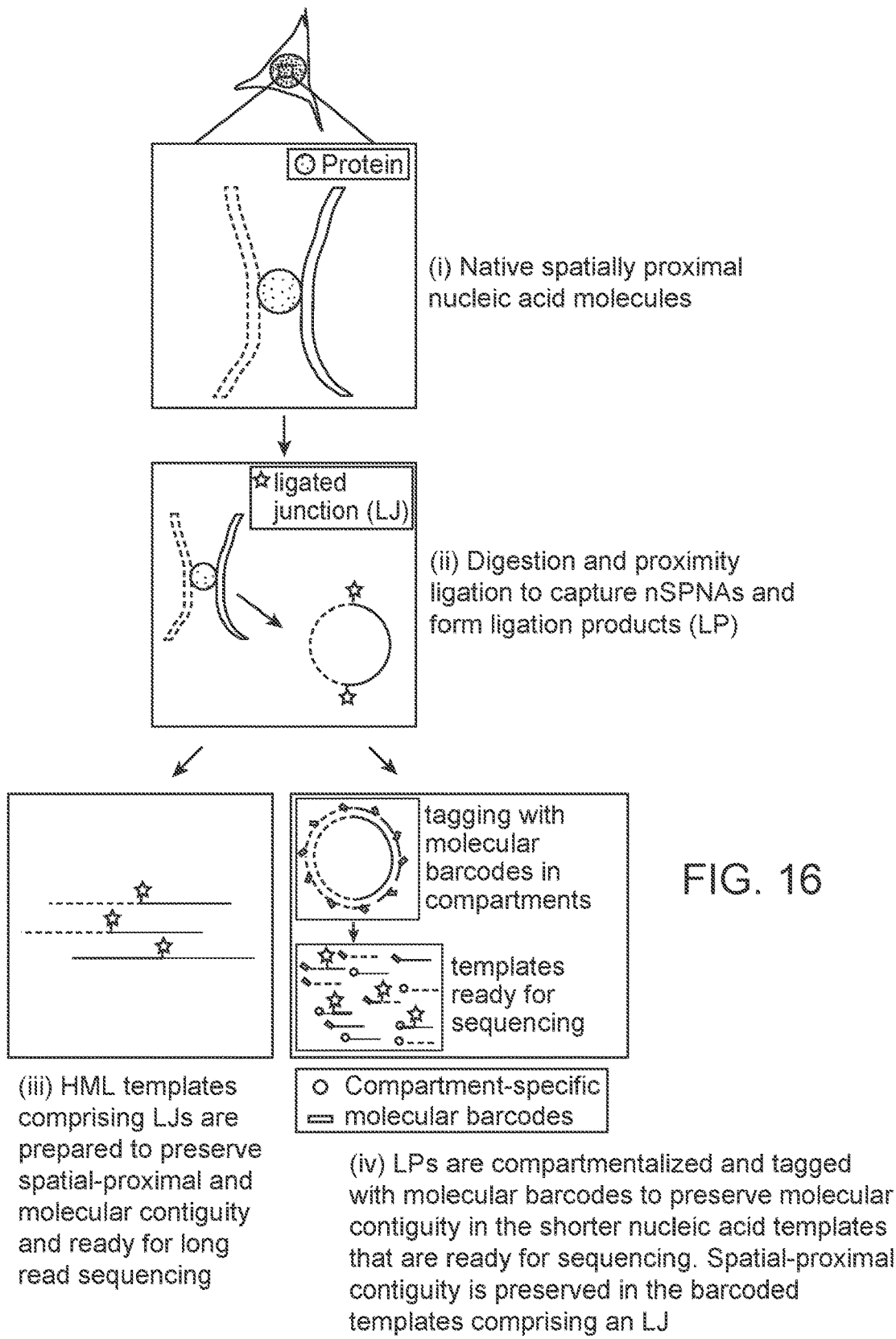
FIG. 16 Preserving spatial-proximal and molecular contiguity in templates derived from LPs from PL methods within CPSP-Prep. In one aspect of CPSP-Prep, nSPNAs are captured using proximity ligation (i-ii) that generates LPs comprising Us to capture spatial-proximal contiguity. Next, molecular contiguity is preserved in the CPSP-prep nucleic acid templates derived from LPs using two example modalities. In (iii) a HML nucleic acid template comprising LJs is prepared to preserve the molecular and spatial-proximal contiguity within LPs and sequenced via long-read sequencing instruments. Preparation of the HML templates will likely depend on which long-read sequencing instrument (e.g. Pacific Bioscience, Oxford Nanopore, or other sequencers) will read the HML template. Alternatively, in (iv), a plurality of LPs are compartmentalized and tagged with compartment-specific molecular barcodes, (e.g. PEP is depicted, but other barcoding approaches can also be applied), fragmented, and prepared as a short nucleic acid template for conventional and predominant short-read sequencing. The molecular barcodes capture molecular contiguity within LPs. For example, the short barcoded nucleic acid templates that share the "rectangular" barcode are inferred to originate from the same LP and thus preserve molecular contiguity, while the barcoded nucleic acid template molecules that share the "circle" barcode are inferred to originate from the same LP, but a different LP than the rectangular barcoded templates. CPSP-Prep nucleic acid templates with the star shape comprise an LJ, and therefore also preserve spatial-proximal contiguity besides the molecular contiguity preserved via barcodes.

Preserving Spatial-Proximal and Molecular Contiguity in CPSP-Prep Nucleic Acid Templates Derived from PL and SSPC Methods:

In one aspect of CPSP-Prep, spatial-proximal contiguity is captured in PL methods by ligating nSPNAs to form LPs (FIG. 2,3). Because these LPs can possess a high molecular length (<1 Kb to >60 Kb, see FIG. 14), there is an opportunity to preserve molecular contiguity within LPs, culminating in preparation of a nucleic acid template that preserves both molecular and spatial-proximal contiguity (see FIG. 10-14 to understand how our innovations enabled preservation of molecular and spatial-proximal contiguity). Indeed, analyses simulating the preservation of molecular contiguity within LPs and subsequent nucleic acid templates indicate that doing so will likely generate improved contiguity (FIG. 7,8). Thus, in these aspect of CPSP-Prep, molecular contiguity is preserved in nucleic acid templates derived from PL methods (e.g. LPs) by either preparing templates with high molecular length (HML), or, by compartmentalizing and tagging LPs with molecular barcodes, whereby the resulting nucleic acid templates comprise barcodes that preserve molecular contiguity (FIG. 16). Regardless of how molecular contiguity is preserved (via long templates or barcodes), spatial-proximal contiguity is preserved in templates comprising Us, as LJs manifest in LPs (except in uLPs), as discussed below.

In one aspect of CPSP-Prep, molecular contiguity is preserved by preparing HML nucleic acid templates derived from PL methods, which can be then sequenced to generate CPSP-Seq data by long-read sequencing instruments (e.g. Pacific Bioscience sequencers). Here, molecular contiguity within LPs is preserved in the template simply by the length of the prepared nucleic acid template, and, spatial-proximal contiguity is preserved in templates that comprise LJs from the LP (FIG. 16iii). In this method, the template can comprise the entire LP, or, a HML fragment derived from the LP. An advantage to this method is that molecular and spatial-proximal contiguity are likely both preserved in the nucleic acid template without the need for subsequent complex experimental workflows (compartmentalizing and tagging) or analysis tools to extract molecular contiguity information preserved in molecular barcodes. On the contrary, disadvantages to this method primarily pertain to how the HML nucleic acid templates are read by long-read sequencing technologies—in the context of this disclosure, we defined sequencing as being predominantly performed via short-read sequencers that sequence ~500 bp, owing to their higher per-base accuracy, affordable cost, and rapid turn-around time. However, preparation of HML nucleic acid templates necessitate these nucleic acid templates to be sequenced by long-read sequencers which currently have the following limitations: (1) the current per-base accuracy of long-read sequencing is sub-optimal for accurate genomic variant detection (i.e. variant accuracy defined as Va is sub-optimal), although this may improve as the capabilities of long-read technologies improve in the future; (2) the current cost per base renders long read sequencing too costly for widespread adoption in large genomes (e.g. human), although this too may improve as the long-read technologies improve; (3) some long-read sequencing instruments mandate nucleic acid templates of certain sizes (e.g. ~20 Kb for Pacific Bioscience sequencers)—i.e., if the cSPNAs within LPs are >20 Kb, then the process of fragmenting LPs to 20 Kb and preparing nucleic acid templates for long-read sequencing may result in some loss of spatial-proximal and molecular contiguity. In sum, nSPNAs are captured via PL methods to form LPs, and molecular contiguity within LPs is preserved via HML nucleic acid templates comprising entire LPs or HML fragments thereof, and long-read sequencing. Additionally, spatial-proximal contiguity is preserved in the template by means of LPs comprising Us. This CPSP-Prep workflow is advantageous due to its simplicity and direct preservation of both spatial-proximal and molecular contiguity in the HML template but may be limited in current practice due to technical constraints associated with long-read sequencing methods.

Figure 17:
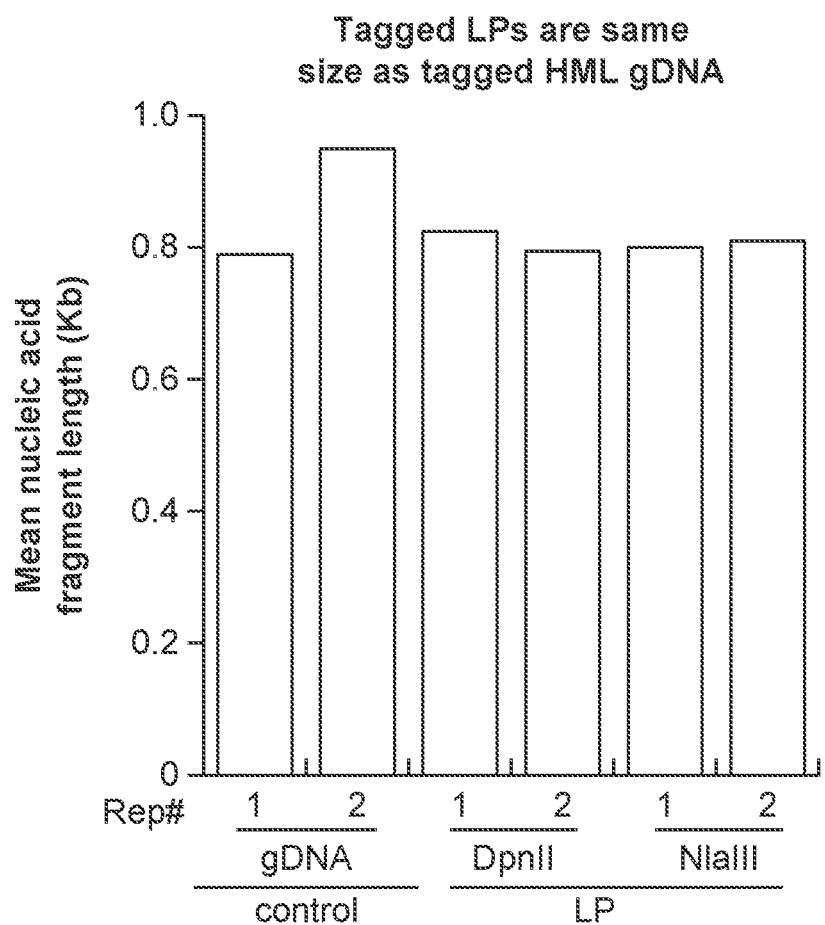
FIG. 17 Feasibility of compartmentalizing and tagging LPs with molecular barcodes via PEP within CPSP-Prep. LPs were prepared via 3C using either DpnII or NlaIII. Then, 1 ng of HMW gDNA (control) and LPs were subjected to compartmentalization in microfluidic droplets, and tagging with molecular barcodes via PEP. In this example, compartmentalization and PEP-based tagging was established via methods reported by 10× Genomics and using 10× Genomics instrument and consumables, however, alternate methods to compartmentalize and tag can also be employed. PEP tags target nucleic acids in a process which simultaneously fragments the target nucleic acid, resulting in an expected nucleic acid molecular length of ~1 Kb. Directly after tagging, the tagged nucleic acid fragments were analyzed for nucleic acid fragment length using gel electrophoresis and plotted along the y-axis.
Figure 18:
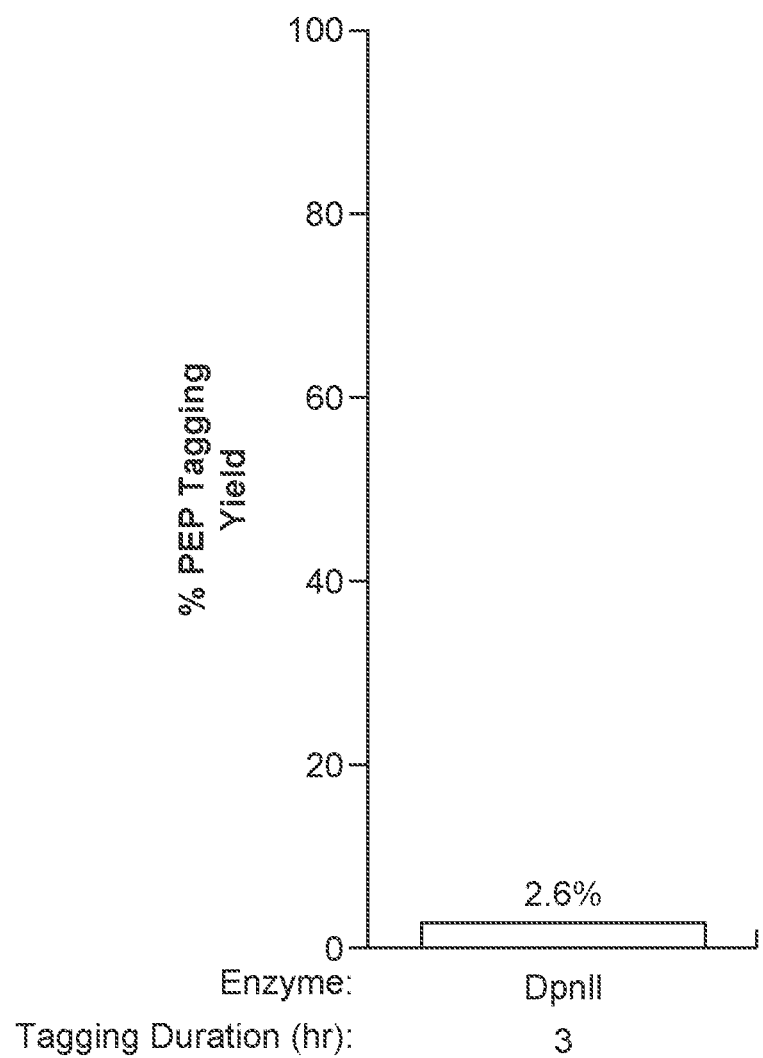
FIG. 18 Limited tagging yield obtained from tagging LPs. To assess the feasibility of compartmentalizing and tagging LPs using PEP, we prepared LPs using an RE known in the art (DpnII) and subjected 1 ng of LPs to standard compartmentalization and tagging via methods reported by 10× Genomics and using 10× Genomics instrument and consumables. As a control, we also subjected 1 ng of HMW gDNA to the same procedure. The nucleic acid fragment yield from tagging LPs and control was measured by a Qubit fluorometer and plotted as the relative nucleic acid fragment yield obtained by tagging compared to HMW gDNA (control). Unexpectedly, the tagging yield from the LPs prepared via DpnII was significantly lower than that of HMW gDNA control, reaching only ~2.6% relative yield and indicating an inefficiency somewhere in the compartmentalization and PEP-based tagging method. These data indicate that LPs prepared using non-optimized methods or standard tagging reaction conditions[23,35] is not well-suited towards preserving the molecular contiguity within LPs presents an initial problem for CPSP-Prep.

In another aspect of CPSP-Prep beginning with LPs, molecular contiguity within LPs is preserved via compartmentalizing LPs and tagging LPs with compartment-specific molecular barcodes, which generates barcoded nucleic acid fragments that are prepared as a template for sequencing (FIG. 16iv). In these methods, LPs are created using a PL method (e.g. 3C, HiC) and then compartmentalized such that the LPs in each compartment represent a sub-haploid quantity of nucleic acids. Once LPs are compartmentalized (e.g. droplets or microtiter plate wells), the LPs are tagged with molecular barcodes and fragmented into shorter nucleic acids and prepared as a template for sequencing (e.g. short-read or long-read). In some cases, the LPs may be fragmented prior to tagging with a molecular barcode, but in other cases (FIG. 16iv) the LPs are tagged with a molecular barcode prior to fragmentation, or in the process of fragmentation (e.g. PEP or transposition). Once the LPs have been prepared as barcoded nucleic acid templates, they are subjected to sequencing. In these methods, the molecular barcode in the nucleic acid template preserves molecular contiguity, and the barcoded nucleic acid templates comprising LJs from the LP preserve spatial-proximal contiguity, thus both forms of contiguity are preserved in the nucleic acid template. Indeed, we have shown feasibility of this approach by subjecting LPs to this molecular contiguity-preserving strategy and demonstrating successful metrics alongside a control sample of high molecular weight (HMW) gDNA. Specifically, we began by preparing LPs using the DpnII RE for digestion and 3C for ligation and subjected them to microfluidic compartmentalization and PEP-based tagging with molecular barcodes and have found the barcoded nucleic acid fragment lengths to be similar to control barcoded nucleic acid fragments derived from tagging HMW gDNA, and, agree with published literature, indicative of successful barcoding (FIG. 17). However, as a second metric to demonstrate success, we measured the nucleic acid fragment yield from this initial tagging reaction. A typical PEP tagging reaction, such as the one used in control HMW gDNA is 3 hr. Surprisingly, the nucleic acid fragment yield from tagging LPs prepared using DpnII RE and 3C was significantly lower than that from tagging HMW gDNA (~2.6% PEP tagging yield relative to control HMW gDNA tagging) (FIG. 18). Such low tagging yield indicates a severely compromised compartmentalization or tagging efficiency, and presents an impasse for CPSP-Prep. We posited that this reduced compartmentalization or tagging efficiency could be a byproduct of the properties of the LPs. We hypothesized that tagging LPs of longer molecular length would result in the improved tagging yield required for CPSP-Prep. Therefore learning from our optimization discussed in FIGS. 12-14, we subjected our optimized NlaIII LPs (FIGS. 12,13) to compartmentalization and tagging using 10× Genomics instrument and reagents and observed expected barcoded fragment lengths (FIG. 17) but a >10-fold increase in tagging yield (FIG. 19i). Even with a 10-fold improvement, yields from NlaIII LP tagging were still only a minor fraction relative to control HMW gDNA tagging, thus unsuitable for CPSP-Prep. To improve yield, we optimized the tagging reaction itself, and extended the duration of the tagging reaction. By doubling the tagging reaction duration for NlaIII LPs, we observed another 4- or 5-fold increase in tagging yield, thereby collectively increasing tagging yield overall ~50-fold compared to initial tagging of DpnII LPs, creating a scenario suitable for CPSP-Prep (FIG. 19ii). Overall, conventional tagging reaction is not optimal for handling LPs and had to be innovatively optimized via increased duration to enable necessary yield.

Figure 20:
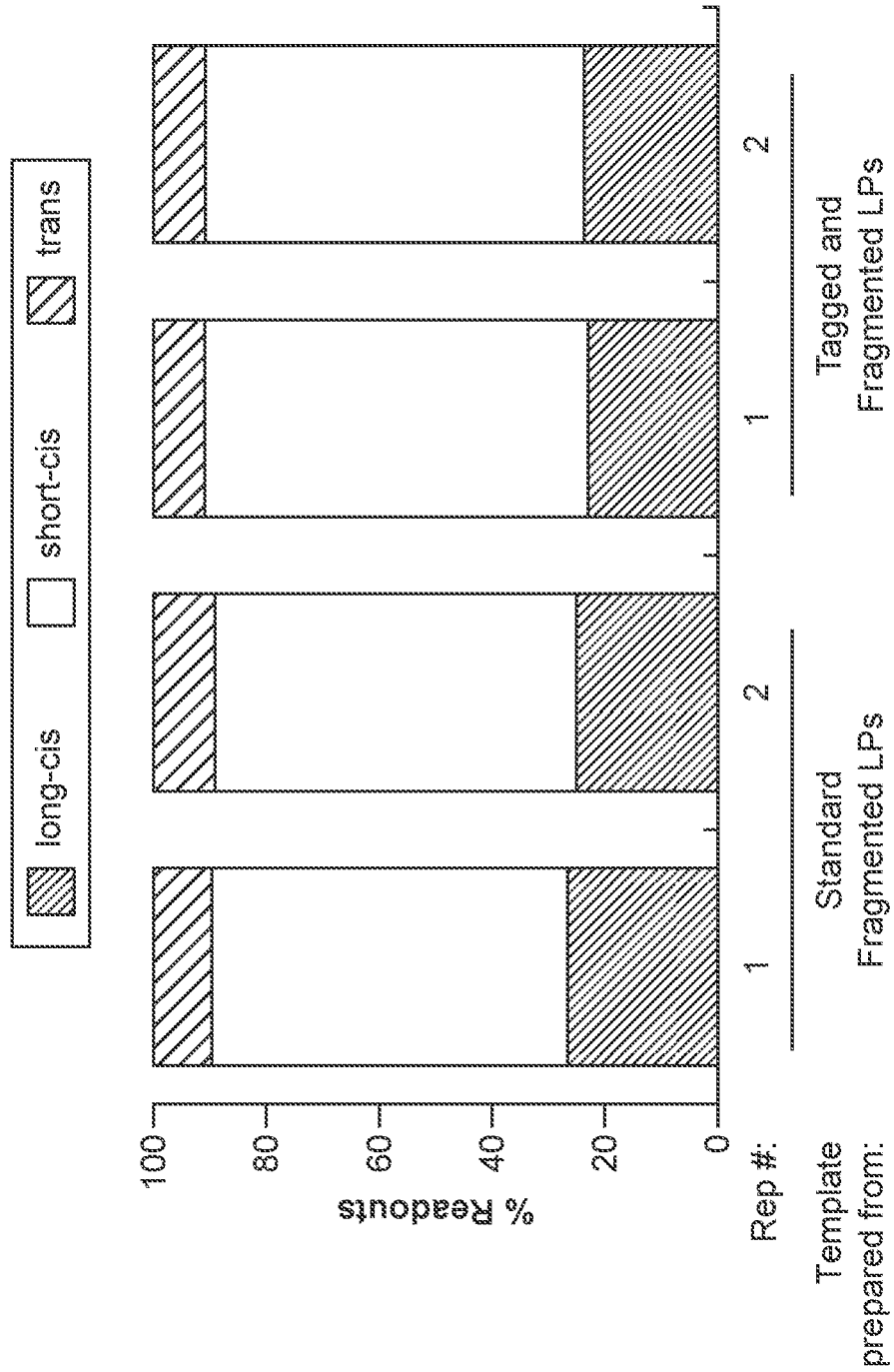
FIG. 20 Feasibility of preserving spatial-proximal & molecular contiguity in CPSP-Seq via compartmentalizing and tagging LPs with molecular barcodes using PEP. To determine whether barcoded CPSP-Prep templates derived from LPs indeed preserve spatial-proximal contiguity, we prepared the barcoded nucleic acid fragments derived from LPs as a template and sequenced via short-reads to generate CPSP-Seq data. As a control, we fragmented the same LPs using standard fragmentation methods in the absence of compartmentalization or tagging. We plot the fraction of cSPNAs in each grouping in sequence data from PL templates and CPSP-Prep templates, and from replicate nucleic acid template preparations. Overall, we show that compartmentalizing and tagging LPs is technically feasible, indicating the potential for preserving molecular contiguity within LPs in addition to preserving spatial-proximal contiguity, laying the foundation for CPSP-Prep.

Lastly, PL methods inform spatial proximity and result in the preparation of nucleic acid templates that preserve spatial-proximal contiguity. As a final assessment of success, we prepared the barcoded nucleic acid fragments derived from LPs as a nucleic acid template and sequenced via short-reads. We then asked whether the spatial proximity information captured by proximity ligation to form LPs is preserved in CPSP-Seq readouts. Indeed, we observe that CPSP-Seq data contain similar spatial proximity information compared to a conventional PL workflow (e.g. 3C) sequence data (FIG. 20), indicating that spatial-proximal contiguity is being preserved post-molecular barcoding in the barcoded nucleic acid templates. The key advantages to this aspect of CPSP-Prep compared to the previous HML template and long-read sequencing approach described above are that (1) molecular barcoding of very large (>60 Kb) LPs likely enables more of the molecular contiguity within LPs to be preserved because some long-read sequencing technologies mandate specific nucleic acid template lengths (e.g. 20 Kb for Pacific Bioscience sequencers) for sequencing; (2) nucleic acid template preparation using molecular barcodes and short-read sequencing benefits from the low-cost economics and high per-base accuracy of short-read sequencing. In contrast, the disadvantages of this aspect of CPSP-Prep may be many-fold: (1) compartmentalizing is experimentally costly or tedious, as it may require sophisticated equipment (e.g. droplet formation) or cumbersome workflows involving dilution of LPs into dozens or hundreds of wells of microtiters plate(s); (2) tagging also comes with several known drawbacks represented in the art that depend on the tagging method. For example, transposition of barcoded oligonucleotides via transposase occurs in such a way that only a maximum of 50% of the barcoded nucleic acid fragments are prepared as nucleic acid templates ready for sequencing[21,24,46]. If applied to CPSP-Prep, the expected 50% minimum loss from each LP will likely result in significant losses of both molecular and spatial-proximal contiguity in the resulting nucleic acid templates. Other tagging methods involve tagging with molecular barcodes in some method of nucleic acid amplification, such as PEP. PEP can suffer from sequence biases and other experimental drawbacks during the tagging reaction, leading to only a fraction of the target nucleic acid being prepared as a nucleic acid template for sequencing. For example, recent publication[35] have estimated that only ~30% of the target nucleic acid is prepared as a nucleic acid template and sequenced. In sum, in this specific CPSP-Prep workflow, nSPNAs are captured via proximity ligation to form LPs, and molecular contiguity within LPs is preserved via compartmentalizing and tagging LPs with molecular barcodes, in such a way that the resulting barcoded nucleic acid templates preserve molecular contiguity in the barcode in addition to the preserved spatial-proximal contiguity as barcoded templates are formed from LPs that comprise Us.

In one aspect of CPSP-Prep, instead of informing spatial proximity via proximity ligation, an alternate approach is designing an exogenous solid-substrate functionalized with molecule(s) to bind and capture nSPNAs to generate cSPNAs in discrete ways—a method disclosed herein and termed solid substrate-mediated proximity capture (SSPC) (FIG. 15). Importantly, most of these SSPC methods only capture nSPNAs (FIGS. 15i and ii) to generate SSPC products, which represents only an intermediate step and requires further methodologies to preserve spatial-proximal contiguity in nucleic acid templates. Unlike aspects of CPSP-Prep that begin with LPs to preserve spatial-proximal contiguity and use barcoding only to preserve molecular contiguity, most SSPC products require compartmentalization and molecular barcoding in order to even preserve spatial-proximal contiguity in the nucleic acid templates. In fact, some variations of SPPC methods preserve both spatial-proximal and molecular contiguity with the same barcode (described below). Very importantly, a fundamental distinction between CPSP-Prep from LPs and SSPC products is that spatial proximity information from PL methods can be captured within a single nucleic acid molecule (e.g. LPs), meaning that a single template molecule can preserve spatial-proximal contiguity. In stark contrast, because SSPC products are a discrete set of cSPNAs, no single cSPNA can inform spatial proximity. Thus, the only way to preserve spatial-proximal contiguity is to preserve information of which set of nSPNAs were bound to and captured by a common solid substrate. A solution to this problem is to compartmentalize and tag the cSPNAs bound to a common solid substrate with a unique compartment-specific molecular barcode (FIG. 21*ii* and *iv*). Therefore, the molecular barcode can be used to infer which cSPNAs were bound to a common solid substrate, thus preserving spatial-proximal contiguity in the nucleic acid template (FIG. 21*iii* and *v*). For example, barcoded oligonucleotides can be ligated to the ends of the compartmentalized SSPC products (FIG. 21*ii*). Once these barcodes are introduced to the terminal ends of the SSPC products, the SSPC products can be subsequently prepared as a HTML template for long-read sequencing. The resulting template preserves molecular contiguity by nature of being a HML template, and preserves spatial-proximal contiguity via molecular barcodes (FIG. 21*iii*). As an alternative approach, compartmentalized SSPC products can be tagged using tagging methods (i.e. PEP, transposition) (FIG. 21*iv*). Once the barcoded nucleic acid fragments have been prepared as a nucleic acid template (FIG. 21*v*), the single barcode sequence within the template now preserves spatial-proximal contiguity because all cSPNAs bound to a common solid substrate will share a common barcode, and, preserves molecular contiguity, as all barcoded nucleic acid templates derived from a single cSPNA will share a common barcode. For example, in FIG. 13*v*, the 'circle' barcode shared amongst the black nucleic acid templates inform molecular contiguity within the black cSPNA (FIG. 21*iv*). The same 'circle' barcode sequence in the black, white, and gray nucleic acid templates preserves spatial-proximal contiguity between the black, white, and dark gray cSPNAs (FIG. 13*iv*).

Methods to Target Nucleic Acids in CPSP-Prep Templates:

The embodiments described above comprise methods for preparing nucleic acid templates from target nucleic acids, where the target nucleic acids are derived from the any target region of interest or from the entire genome of the nucleic acids source (where contiguity is defined per chromosome, including homologous nucleic acids). To adopt CPSP-Prep to a target region of interest, a target enrichment and selection procedure may be performed at various stages throughout CPSP-Prep, such as during the tagging reaction, or, after the nucleic acid template has been prepared by CPSP-Prep, but prior to sequencing.

Figure 21:
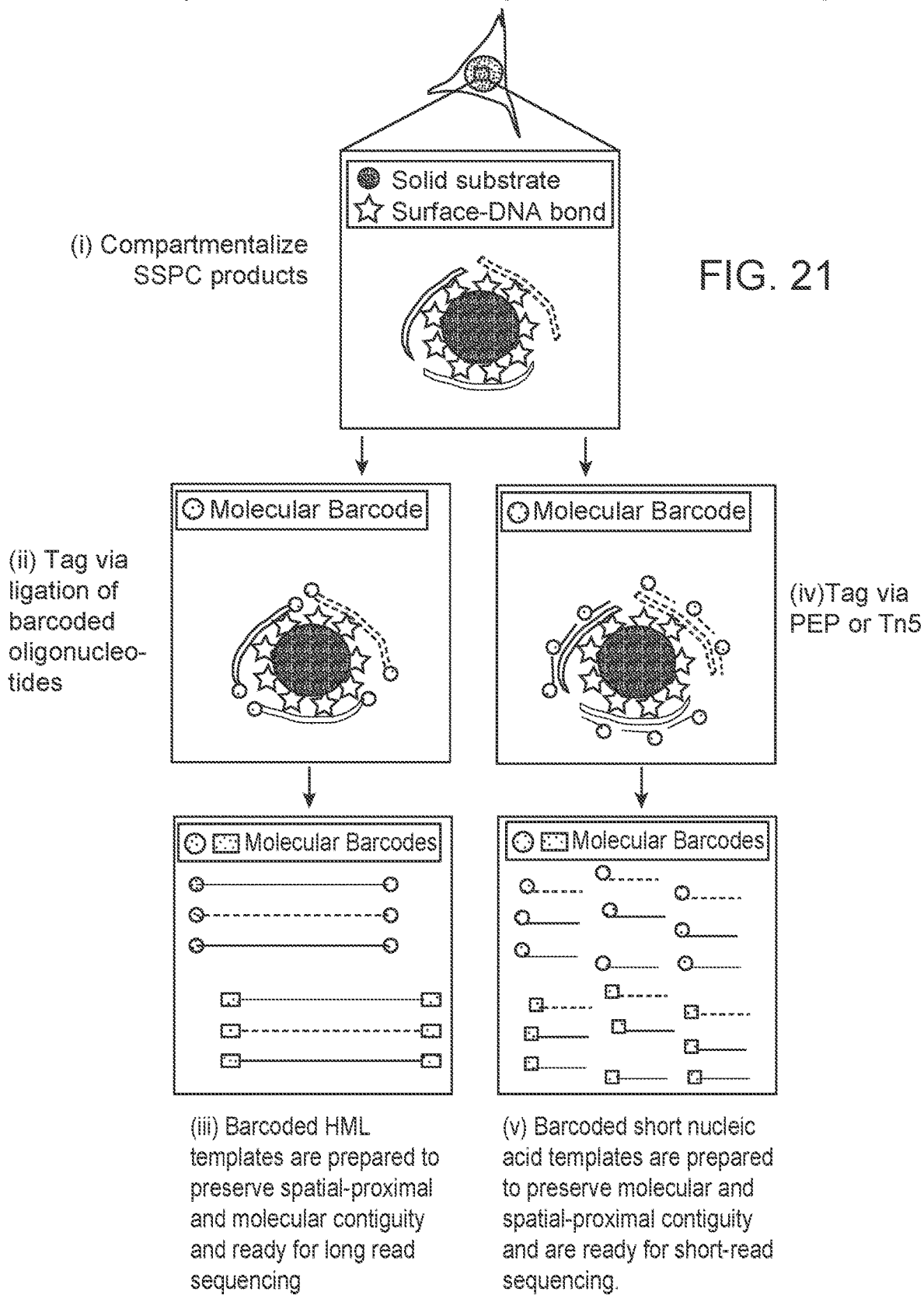
FIG. 21 Preserving spatial-proximal and molecular contiguity in templates derived from SSPC products within CPSP-Prep. In one aspect of CPSP-Prep, nSPNAs are captured to generate cSPNAs using SSPC methods to generate SSPC products. When barcodes are not integrated as part of nSPNA capture method (e.g.
Figure 22:
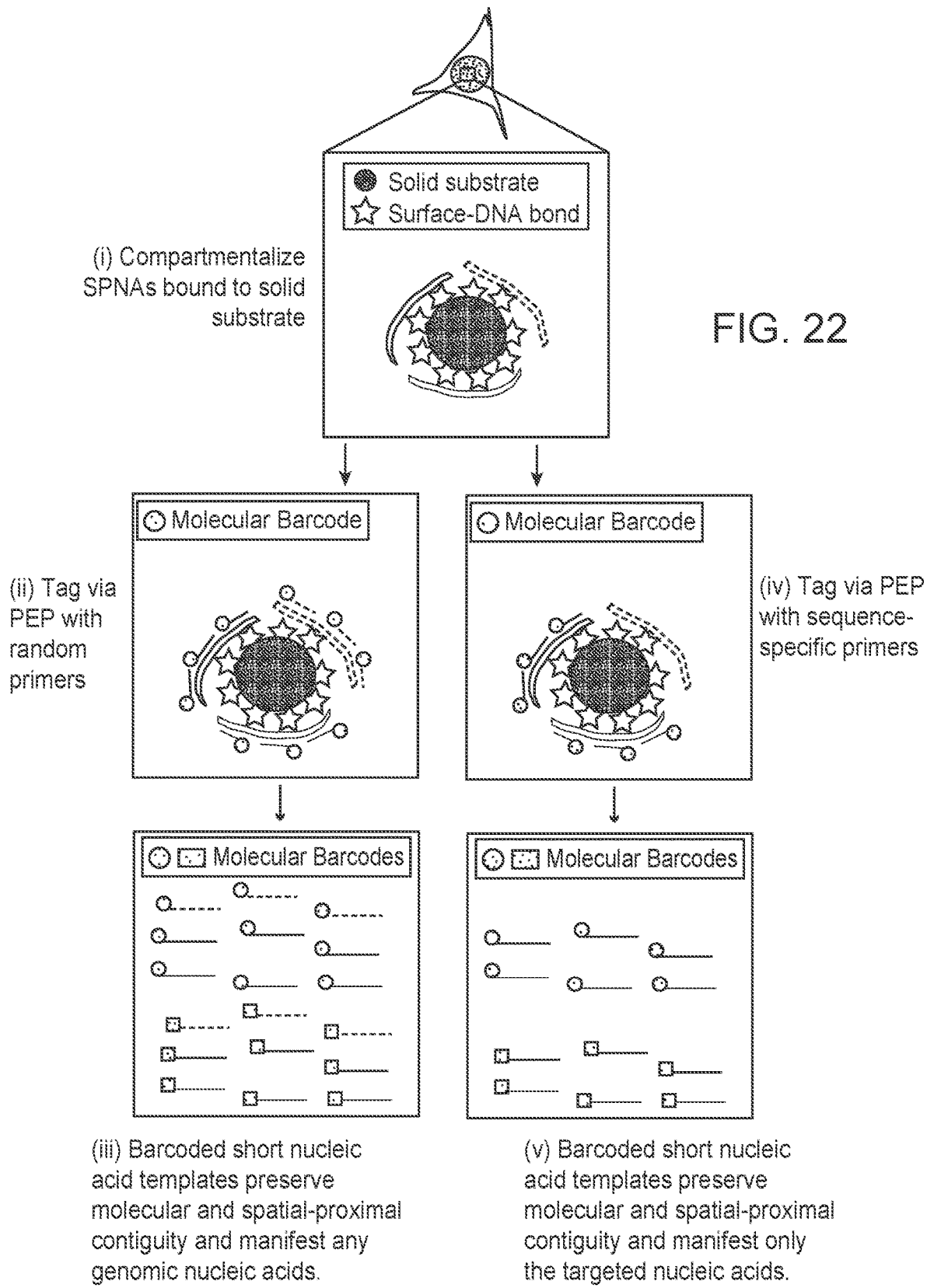
FIG. 22 Target selection via tagging with sequence-specific primers. To adapt CPSP-Prep towards analyses of targeted nucleic acids, cSPNAs can be tagged using sequence-specific primers during PEP. To illustrate one example of the methodology, (i) SSPC products are first compartmentalized. In the non-targeted PEP tagging method, randomly annealing primers anneal to and extend along all the SSPC products in the compartment, and (iii) barcoded fragments derived from all SSPC products are prepared as a nucleic acid template and sequenced. In the targeted PEP tagging method, (iv) sequence-specific annealing primers anneal to and extend along only the targeted SSPC products in the compartment, and (v) barcoded fragments derived from those targeted SSPC products are prepared as a nucleic acid template and sequenced. In both the targeted and non-targeted nucleic acid templates, the barcode still preserves spatial-proximal and molecular contiguity.

In all aspects of CPSP-Prep, a final nucleic acid template is prepared that preserves spatial-proximal and molecular contiguity, and is ready for sequencing. For example, a method to prepare a targeted nucleic acid template is by applying oligonucleotide hybridization and affinity purification to the nucleic acid template[47] (e.g. biotinylated oligonucleotides and streptavidin beads). To apply such a method to nucleic acid templates prepared by CPSP-Prep, oligonucleotides (also termed "probes") can be designed that are reverse complimentary to the targeted nucleic acid regions and bound to affinity purification marker (e.g. biotin). The probes are then hybridized to the CPSP-Prep templates, and then affinity purification is used to purify the probe:template duplexes, resulting in an enriched nucleic acid template comprised of only the targeted nucleic acids, but still informing spatial-proximal and molecular contiguity. While hybridization and affinity purification is the most common method, other methods for target enrichment may be utilized during CPSP-Prep. For example, target enrichment can occur during the PEP tagging reaction in some embodiments of CPSP-Prep (FIGS. 16 and 21). Rather than using randomly annealing primers such that most target nucleic acids can be tagged via PEP and prepared as a template for sequencing, one can design the barcoded primers such that the primer annealing sequence(s) are a reverse-compliment to a specific region(s) of target nucleic acids (FIG. 22). By this design, the barcoded primers would only anneal to target nucleic acids that are reverse-complimentary to the primer annealing sequence, and thus only the targeted nucleic acids would become tagged with molecular barcodes and prepared as a template for sequencing. The final barcoded nucleic acid templates would still preserve spatial-proximal contiguity and molecular contiguity using the same principles previously described for CPSP-Prep templates (FIGS. 16 and 21).

Figure 23:
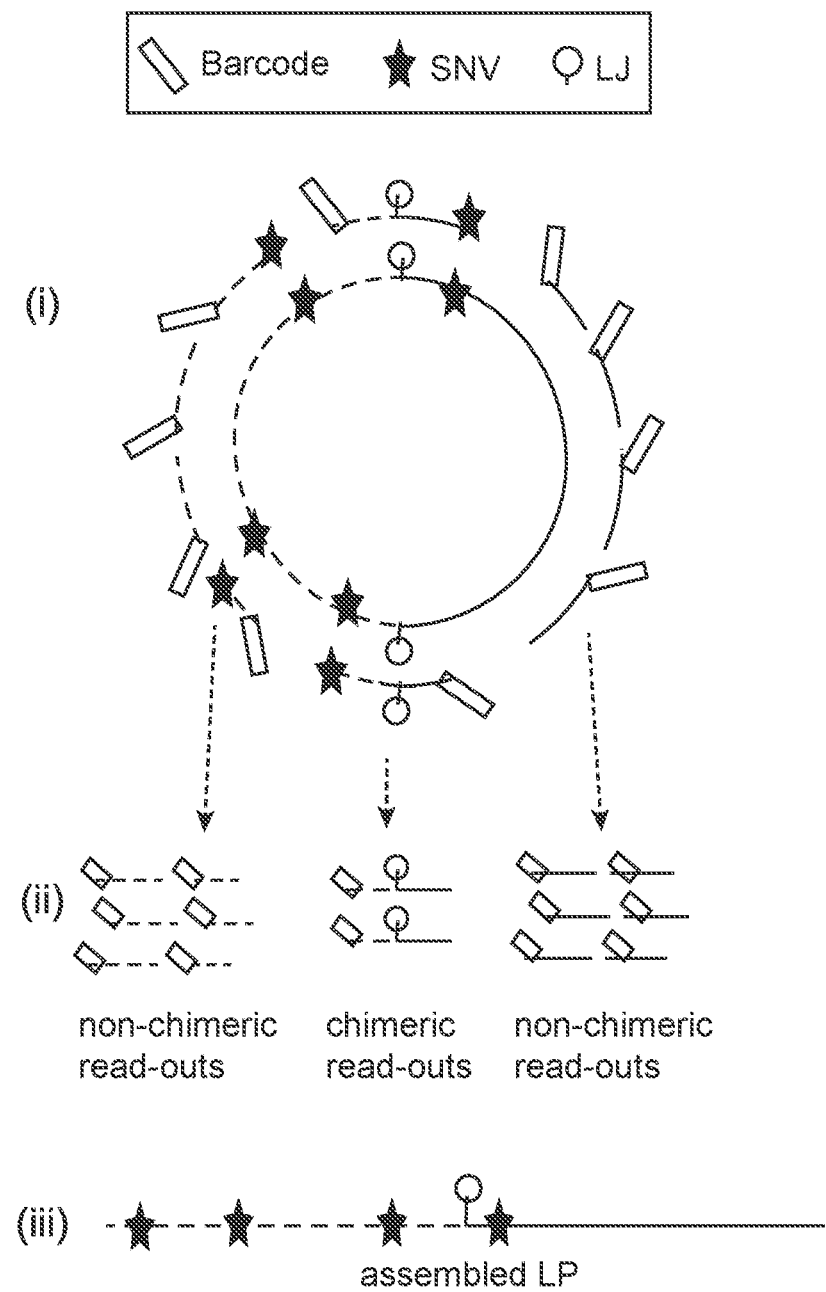
FIG. 23 Analyzing barcodes to preserve molecular contiguity in CPSP-Seq. In some aspects of CPSP-Prep, cSPNAs are compartmentalized and tagged with compartment-specific molecular barcodes. Depicted here is an example (i) is one embodiment of CPSP-Prep where nSPNAs have been captured by a PL method to form LPs, which were subsequently compartmentalized and tagged with molecular barcodes. Once the barcoded fragments have been prepared as a template and sequenced, molecular contiguity is preserved in the barcode of the CPSP-Seq readouts, and spatial-proximal contiguity is preserved in the readouts that comprise an LJ. One way to analyze the CPSP-Seq data and leverage both forms of contiguity preserved in the readouts is to (ii) assemble each contiguous nSPNA within the LP to form contigs (e.g. gray and black contigs) using the short-cis readouts (see FIG. 20 caption for definitions of short-cis and long-cis) that may not comprise an LJ (depicted as "non-chimeric"), and then utilize the "chimeric" read-outs comprising two non-contiguous nSPNAs and an LJ, and sharing the same molecular barcode as the non-chimeric readouts, to create inter-contig links to assemble the LP. The combination of intra- and inter-contig assembly via non-chimeric and chimeric readouts is critical for extracting optimal contiguity information from the CPSP-Seq data.

Approaches for CPSP-Seq Data Analysis:

In some aspects of CPSP-Prep, molecular and spatial-proximal contiguity is preserved in HML templates and the contiguous nucleic acid sequence therefrom is determined directly and accurately using long-read sequencing, while, in other aspects of CPSP-Prep, tagging with molecular barcodes is used to preserve molecular contiguity within the cSPNAs, and the resulting barcoded short nucleic acid templates are sequenced using short-read sequencing. To extract and leverage the molecular contiguity information preserved in the sequence read-outs, as manifested in the templates, one must use the barcodes to assemble the target nucleic acid regions to their natural form prior to tagging and fragmentation. In cases where the natural form is a long contiguous nucleic acid molecule (e.g. in SSPC products), known tools could likely be used[35,48]. However, in cases where the natural form is a non-contiguous artificially ligated nucleic acid molecule (i.e. LPs that comprise multiple chimeric Us between cSPNAs), known tools would probably be deficient. This is because these tools expect contiguous target nucleic acids, often ranging from 50-100 Kb in length. LPs deviate from this expectation, as nSPNAs captured by PL methods can be linearly discontinuous and distal, and with a wide range of linear distances (<1 Kb to >200 Mb), or even originate from different chromosomes. The unique challenge here is to assemble the individual discontinuous LPs into their natural form, prior to tagging. One solution to this problem is a novel "chimeric-aware" LP assembly algorithm (FIG. 23). Briefly, we propose to utilize de bruijn graph principles[49] to assemble the contiguous nSPNAs within each LP (FIG. 23) into contiguity blocks based on barcode and overlap information manifested in barcoded read-outs (FIG. 23*ii*, "non-chimeric"). Excluding non-contiguous nSPNAs ("chimeric" short read-outs containing the ligation junctions, for example) from this initial step is key because such chimeric read-outs violate an assumption that overlapping bases and shared barcodes between short-reads originate from a single contiguous target nucleic acid region—in truth, such chimers manifest non-contiguous ligation junctions. Following initial generation of contiguity blocks, barcoded chimeric reads can then be used to assemble the non-contiguous blocks that originate from an individual LP (FIG. 23*iii*). For this approach to work, it is critical that the per-base coverage is high for all nucleic acids in the LP, as manifested in the nucleic acid template—specifically, if chimeric readouts comprising Us are missed or poorly represented in sequencing readouts, then assembling of the entirety of individual LP becomes challenging. In this case, only partial LP sequences may be determined. A final consideration for analysis of barcoded CPSP-Seq data is the intrinsic probability of two homologous target nucleic acid regions ending up in the same compartment and thus manifesting the same barcode. This problem is determined by how much DNA is partitioned into each compartment and the genome size, and is a known drawback for approaches requiring compartmentalization and molecular barcoding. Overall, reconstructing cSPNAs (either entire or partial) from above mentioned analyses or otherwise from CPSP-Seq data can inform haplotype phase of target nucleic acids and other measurements of contiguity such as de novo assembly of target nucleic acids, and metagenomic assemblies of species and sub-strains. In addition, because reconstructing cSPNAs also informs spatial conformation of target nucleic acids, additional applications such as conformation and topology studies, and structural rearrangement analyses (e.g. gene fusions) are feasible as before mentioned.

REFERENCES

1 Hayden, E. C. Technology: The $1,000 genome. Nature 507, 294-295, doi:10.1038/507294a (2014).
2 Kayser, M. & de Knijff, P. Improving human forensics through advances in genetics, genomics and molecular biology. Nature reviews. Genetics 12, 179-192, doi: 10.1038/nrg2952 (2011).
3 Lander, E. S. et al. Initial sequencing and analysis of the human genome. Nature 409, 860-921, doi:10.1038/35057062 (2001).
4 Padmanabhan, R., Mishra, A. K., Raoult, D. & Fournier, P. E. Genomics and metagenomics in medical microbiology. Journal of microbiological methods 95, 415-424, doi:10.1016/j.mimet.2013.10.006 (2013).
5 Ronald, P. C. Lab to farm: applying research on plant genetics and genomics to crop improvement. PLoS biology 12, e1001878, doi:10.1371/journal.pbio.1001878 (2014).
6 Shendure, J. & Lieberman Aiden, E. The expanding scope of DNA sequencing. Nature biotechnology 30, 1084-1094, doi:10.1038/nbt.2421 (2012).
7 Venter, J. C. et al. The sequence of the human genome. Science 291, 1304-1351, doi:10.1126/science.1058040 (2001).
8 Wang, L., McLeod, H. L. & Weinshilboum, R. M. Genomics and drug response. The New England journal of medicine 364, 1144-1153, doi:10.1056/NEJMra1010600 (2011).
9 Yang, Y., Xie, B. & Yan, J. Application of next-generation sequencing technology in forensic science. Genomics, proteomics & bioinformatics 12, 190-197, doi:10.1016/j.gpb.2014.09.001 (2014).
10 Cremer, T. & Cremer, M. Chromosome territories. Cold Spring Harbor perspectives in biology 2, a003889 (2010).
11 Williamson, I. et al. Spatial genome organization: contrasting views from chromosome conformation capture and fluorescence in situ hybridization. Genes & development 28, 2778-2791 (2014).
12 Dekker, J., Rippe, K., Dekker, M. & Kleckner, N. Capturing chromosome conformation. Science 295, 1306-1311 (2002).
13 Simonis, M. et al. Nuclear organization of active and inactive chromatin domains uncovered by chromosome conformation capture-on-chip (4C). Nature genetics 38, 1348-1354 (2006).
14 De Laat, W. & Grosveld, F. (Google Patents, 2014).
15 Dostie, J. et al. Chromosome Conformation Capture Carbon Copy (5C): a massively parallel solution for mapping interactions between genomic elements. Genome research 16, 1299-1309 (2006).
16 Dekker, J. & Dostie, J. (Google Patents, 2017).
17 Lieberman-Aiden, E. et al. Comprehensive mapping of long-range interactions reveals folding principles of the human genome. Science 326, 289-293 (2009).
18 Dekker, J. et al. (Google Patents, 2016).
19 Kalhor, R., Tjong, H., Jayathilaka, N., Alber, F. & Chen, L. Genome architectures revealed by tethered chromosome conformation capture and population-based modeling. Nature biotechnology 30, 90-98 (2012).
20 Chen, L. & Kalhor, R. (Google Patents, 2010).
21 Adey, A. et al. In vitro, long-range sequence information for de novo genome assembly via transposase contiguity. Genome research 24, 2041-2049 (2014).
22 Amini, S. et al. Haplotype-resolved whole-genome sequencing by contiguity-preserving transposition and combinatorial indexing. Nature genetics 46, 1343-1349 (2014).
23 Zheng, G. X. et al. Haplotyping germline and cancer genomes with high-throughput linked-read sequencing. Nature biotechnology 34, 303-311 (2016).
24 Zhang, F. et al. Haplotype phasing of whole human genomes using bead-based barcode partitioning in a single tube. Nature biotechnology 35, 852-857 (2017).
25 Zook, J. M. et al. Extensive sequencing of seven human genomes to characterize benchmark reference materials. Scientific data 3 (2016).
26 McKenna, A. et al. The Genome Analysis Toolkit: a MapReduce framework for analyzing next-generation DNA sequencing data. Genome research 20, 1297-1303 (2010).
27 Eberle, M. A. et al. A reference data set of 5.4 million phased human variants validated by genetic inheritance from sequencing a three-generation 17-member pedigree. Genome research 27, 157-164 (2017).
28 Rao, S. S. et al. A 3D map of the human genome at kilobase resolution reveals principles of chromatin looping. Cell 159, 1665-1680, doi:10.1016/j.cell.2014.11.021 (2014).
29 DePristo, M. A. et al. A framework for variation discovery and genotyping using next-generation DNA sequencing data. Nature genetics 43, 491-498 (2011).
30 Edge, P., Bafna, V. & Bansal, V. HapCUT2: robust and accurate haplotype assembly for diverse sequencing technologies. Genome research 27, 801-812 (2017).
31 Naumova, N., Smith, E. M., Zhan, Y. & Dekker, J. Analysis of long-range chromatin interactions using Chromosome Conformation Capture. Methods 58, 192-203 (2012).
32 Tolhuis, B., Palstra, R.-J., Splinter, E., Grosveld, F. & de Laat, W. Looping and interaction between hypersensitive sites in the active β-globin locus. Molecular cell 10, 1453-1465 (2002).
33 Soler, E. et al. The genome-wide dynamics of the binding of Ldb1 complexes during erythroid differentiation. Genes & development 24, 277-289 (2010).
34 Stadhouders, R. et al. Dynamic long-range chromatin interactions control Myb proto-oncogene transcription during erythroid development. The EMBO journal 31, 986-999 (2012).
35 Weisenfeld, N. I., Kumar, V., Shah, P., Church, D. M. & Jaffe, D. B. Direct determination of diploid genome sequences. Genome research 27, 757-767 (2017).
36 Dudchenko, O. et al. De novo assembly of the Aedes aegypti genome using Hi-C yields chromosome-length scaffolds. Science 356, 92-95 (2017).

37 Bickhart, D. M. et al. Single-molecule sequencing and chromatin conformation capture enable de novo reference assembly of the domestic goat genome. *Nature genetics* 49, 643-650 (2017).
38 Kaplan, N. & Dekker, J. High-throughput genome scaffolding from in vivo DNA interaction frequency. *Nature biotechnology* 31, 1143-1147 (2013).
39 Burton, J. N. et al. Chromosome-scale scaffolding of de novo genome assemblies based on chromatin interactions. *Nature biotechnology* 31, 1119-1125 (2013).
40 Selvaraj, S., J, R. D., Bansal, V. & Ren, B. Whole-genome haplotype reconstruction using proximity-ligation and shotgun sequencing. *Nature biotechnology* 31, 1111-1118, doi:10.1038/nbt.2728 (2013).
41 Selvaraj, S., Schmitt, A. D., Dixon, J. R. & Ren, B. Complete haplotype phasing of the MHC and KIR loci with targeted HaploSeq. *BMC genomics* 16, 900, doi: 10.1186/s12864-015-1949-7 (2015).
42 Ren, B., Selvaraj, S. & Dixon, L. (Google Patents, 2014).
43 Beitel, C. W. et al. Strain- and plasmid-level deconvolution of a synthetic metagenome by sequencing proximity ligation products. *Peer J* 2, e415 (2014).
44 Burton, J. N., Liachko, I., Dunham, M. J. & Shendure, J. Species-level deconvolution of metagenome assemblies with Hi-C-based contact probability maps. *G3: Genes, Genomes, Genetics* 4, 1339-1346 (2014).
45 Genomics, X. Genome Reagent Kis v2 User Guide.
46 Adey, A. et al. Rapid, low-input, low-bias construction of shotgun fragment libraries by high-density in vitro transposition. *Genome biology* 11, R119 (2010).
47 Gnirke, A. et al. Solution hybrid selection with ultra-long oligonucleotides for massively parallel targeted sequencing. *Nature biotechnology* 27, 182-189 (2009).
48 Zheng, G. X. et al. Haplotyping germline and cancer genomes using high-throughput linked-read sequencing. *Nature biotechnology* 34, 303 (2016).
49 Compeau, P. E., Pevzner, P. A. & Tesler, G. How to apply de Bruijn graphs to genome assembly. *Nature biotechnology* 29, 987-991 (2011).

Provided hereafter are non-limiting examples of certain embodiments of the technology.

A1. A method for preparing library nucleic acid templates, comprising:
contacting isolated nucleic acid with solid phase elements, which contacting generates complexes between the solid phase elements and the isolated nucleic acid; and
reacting the complexes with one or more reagents, which one or more reagents:
compartmentalize the complexes into compartments, thereby providing compartmentalized complexes; and
fragment and attach barcode oligonucleotides to nucleic acid of the compartmentalized complexes for production of barcoded template nucleic acid, wherein:
the barcode oligonucleotides in the barcoded template nucleic acid in one of the compartments is different than the barcode oligonucleotides in the barcoded template nucleic acid in other compartments, and
barcodes in the barcode oligonucleotides preserve spatial-proximal contiguity information or preserve spatial-proximal contiguity information and molecular contiguity information for the isolated nucleic acid of the complexes.

A2. The method of embodiment A1, wherein the isolated nucleic acid comprises chromatin.
A3. The method of embodiment A1 or A2, wherein the isolated nucleic acid comprises substantially a whole genome or portions thereof.
A4. The method of any one of embodiments A1 to A3, wherein the isolated nucleic acid is obtained from cell(s).
A4.1. The method of any one of embodiments A1 to A3, wherein the isolated nucleic acid is from formalin-fixed paraffin-embedded cells, nuclei or nuclear matrix.
A5. The method of any one of embodiments A1 to A3, wherein the isolated nucleic acid is obtained from nuclei.
A6. The method of any one of embodiments A1 to A3, wherein the isolated nucleic acid is obtained from a nuclear matrix.
A7. The method of any one of embodiments A1 to A6, wherein the complexes comprise isolated nucleic acid of 25 Kb or greater.
A7.1. The method of any one of embodiments A1 to A6, wherein the complexes comprise isolated nucleic acid greater than 60 Kb.
A8. The method of any one of embodiments A1 to A7.1, wherein the solid phase elements are beads.
A9. The method of any one of embodiments A1 to A8, wherein the solid phase elements comprise a nucleic acid crosslinking agent.
A10. The method of any one of embodiments A1 to A8, wherein the solid phase elements comprise an affinity purification molecule.
A11. The method of embodiment A10, wherein the isolated nucleic acid is labeled with an affinity purification marker.
A12. The method of any one of embodiments A1 to A7.1, wherein the one or more reagents that fragment and attach barcode oligonucleotides virtually compartmentalize the complexes.
A13. The method of embodiment A12, wherein the solid phase elements comprise the one or more reagents that fragment and attach barcode oligonucleotides.
A14. The method of embodiment A13, wherein the one or more reagents that fragment and attach barcode oligonucleotides comprise a transposon with a uniquely barcoded oligonucleotide and a transposase.
A15. The method of embodiment A14, wherein the transposase is Tn5.
A16. The method of any one of embodiments A1 to A11, wherein the one or more reagents that compartmentalize the complexes comprise a microfluidic compartmentalization device that produces microfluidic droplets.
A17. The method of any one of embodiments A1 to A11, wherein the one or more reagents that compartmentalize the complexes comprise microtiter plate wells into which complexes are diluted.
A18. The method of any one of embodiments A1 to A11, A16 and A17, wherein a barcode oligonucleotide is integrated into the isolated nucleic acid of the compartmentalized complexes in a nucleic acid amplification reaction.
A18.1. The method of any one of embodiments A1 to A11, A16 and A17, wherein the isolated nucleic acid of the compartmentalized complexes is amplified in an amplification reaction and barcodes are ligated onto the amplified nucleic acid.

A19. The method of any one of embodiments A1 to A11, A16 and A17, wherein the nucleic acid of the compartmentalized complexes is fragmented and barcode oligonucleotides are attached by primer extension polymerization (PEP) for production of barcoded template nucleic acid.

A20. The method of embodiment A19, wherein the primer extension polymerization (PEP) is for a period of 3 hours or greater.

A21. The method of embodiment A20, wherein the primer extension polymerization (PEP) is for a period of 6 hours or greater.

A22. The method of any one of embodiments A19 to A21, wherein the primer extension polymerization (PEP) comprises random primers.

A23. The method of any one of embodiments A1 to A11, A16 and A17, wherein the nucleic acid of the compartmentalized complexes is fragmented and the barcode oligonucleotides are attached to the fragmented nucleic acid by ligation.

A24. The method of any one of embodiments A1 to A23, wherein the fraction of the barcoded templates that are long-cis templates is greater than 2%.

A25. The method of embodiment A24, wherein the fraction is greater than 5%.

A26. The method of embodiment A25, wherein the fraction is greater than 10%.

A27. The method of embodiment A26, wherein the fraction is greater than 15%.

A28. The method of embodiment A27, wherein the fraction is greater than 20%.

A29. The method of embodiment A28, wherein the fraction is greater than 25%.

A30. The method of any one of embodiments A19 to A21, wherein isolated nucleic acid in the compartmentalized complexes is enriched for a specific target by primer extension polymerization (PEP) comprising primers that specifically hybridize to specific target polynucleotides in the isolated nucleic acid.

A31. The method of any one of embodiments A1 to A29, wherein the barcoded templates are enriched for a specific target polynucleotide.

A32. The method of embodiment A31, wherein barcoded templates are enriched by affinity purification.

A33. The method of embodiment A32, wherein the affinity purification comprises an affinity purification molecule attached to a target specific oligonucleotide that hybridizes to the target specific polynucleotide.

A34. The method of any one of embodiments A30 to A33, wherein the specific target polynucleotide comprises a locus or portion thereof.

A35. The method of any one of embodiments A30 to A33, wherein the specific target polynucleotide comprises a gene or portion thereof.

A36. The method of any one of embodiments A30 to A33, wherein the specific target polynucleotide comprises an exome or portions thereof.

A37. The method of any one of embodiments A1 to A36, comprising sequencing the barcoded templates using a sequencer that generates sequence reads of about 2 kilobases or greater.

A38. The method of any one of embodiments A1 to A36, comprising sequencing the barcoded templates using a sequencer that generates sequence reads of about 500 bases or less.

A39. The method of embodiments A37 or A38, wherein the sequence reads are generated at a sequencing depth of 30× or less.

A40. The method of any one of embodiments A37 to A39, comprising determining contiguity information, in part, based on the sequence reads of barcode sequences in the barcode oligonucleotides.

A41. The method of embodiments A40, comprising determining haplotype information for the isolated nucleic acid using the contiguity information.

A42. The method of embodiment A40, comprising determining ordering and orientation of contigs for the isolated nucleic acid using the contiguity information.

A43. The method of embodiment A40, comprising determining deconvolution of a mixture of genomes for the isolated nucleic acid using the contiguity information.

A44. The method of embodiment A40, comprising determining conformation and folding patterns of the isolated nucleic acid using the contiguity information.

A45. The method of embodiment A40, comprising determining genomic variants of the isolated nucleic acid using the contiguity information.

A46. The method of embodiment A45, wherein the genomic variants comprise single nucleotide variants, insertions, deletion, inversions, translocations, and copy number variations, and other types of genome variants.

B1. A method for preparing library nucleic acid templates, comprising:
  reacting isolated nucleic acid with a first set of reagents that generate proximity ligated nucleic acid molecules; and
  reacting the proximity ligated nucleic acid molecules with a second set of reagents that:
    compartmentalize the proximity ligated nucleic acid molecules into compartments, thereby providing compartmentalized nucleic acid;
    fragment and attach barcode oligonucleotides to the compartmentalized nucleic acid molecules to produce barcoded templates, wherein the barcode oligonucleotides attached to the barcoded templates in one of the compartments is different than the barcode oligonucleotides attached to the barcoded templates in other compartments and barcodes in the barcode oligonucleotides preserve molecular contiguity information for proximity ligated molecules.

B2. The method of embodiment B1, wherein the isolated nucleic acid comprises chromatin.

B3. The method of embodiment B1 or B2, wherein the isolated nucleic acid comprises substantially a whole genome or portions thereof.

B4. The method of any one of embodiments B1 to B3, wherein the isolated nucleic acid is obtained from cells.

B4.1. The method of any one of embodiments B1 to B3, wherein the isolated nucleic acid is from formalin-fixed paraffin-embedded cells, nuclei or nuclear matrix.

B5. The method of any one of embodiments B1 to B3, wherein the isolated nucleic acid is obtained from nuclei.

B6. The method of any one of embodiments B1 to B3, wherein the isolated nucleic acid is obtained from a nuclear matrix.

B7. The method of any one of embodiments B1 to B6, wherein the proximity ligated nucleic acid molecules comprise nucleic acid molecules of 25 Kb or greater.

B7.1. The method of any one of embodiments B1 to B6, wherein the proximity ligated nucleic acid molecules comprise nucleic acid molecules greater than 60 Kb.

B8. The method of any one of embodiments B1 to B7.1, wherein the fraction of the barcoded templates that are long-cis templates is greater than 2%.

B9. The method of embodiment B8, wherein the fraction is greater than 5%.

B10. The method of embodiment B9, wherein the fraction is greater than 10%.

B11. The method of embodiment B10, wherein the fraction is greater than 15%.

B12. The method of embodiment B11, wherein the fraction is greater than 20%.

B13. The method of embodiment B12, wherein the fraction is greater than 25%.

B14. The method of any one of embodiments B1 to B13, wherein the first set of reagents comprise a reagent that solubilizes chromatin and the isolated nucleic acid is reacted with the reagent for greater than 10 minutes, whereby solubility is optimized.

B15. The method of embodiment B14, wherein the reagent that solubilizes chromatin is sodium dodecyl sulfate (SDS).

B16. The method of embodiment B14 or B15, wherein the isolated nucleic acid is reacted with the reagent for greater than 10 minutes but less than 80 minutes.

B17. The method of any one of embodiments B14 to B16, wherein the isolated nucleic acid is reacted with the reagent for about 40 minutes.

B18. The method of any one of embodiments B1 to B13, wherein the first set of reagents comprise a restriction enzyme that produces a greater fraction of the barcoded templates that are long-cis templates relative to the restriction enzyme HindIII, DpnII, MboI or an equivalent restriction enzyme, whereby the restriction enzyme is optimized to preserve spatial-proximal contiguity.

B19. The method of embodiment B18, wherein the optimized restriction enzyme is NlaIII.

B20. The method of any one of embodiments B1 to B13, wherein the first set of reagents comprise a reagent that solubilizes chromatin and the isolated nucleic acid is reacted with the reagent for greater than 10 minutes, whereby solubility is optimized and a restriction enzyme that produces a greater fraction of the barcoded templates that are long-cis templates relative to the restriction enzyme HindIII, DpnII, MboI or an equivalent restriction enzyme, whereby the restriction enzyme is optimized to preserve spatial-proximal contiguity.

B21. The method of embodiment B20, wherein the reagent that solubilizes chromatin is sodium dodecyl sulfate (SDS), the isolated nucleic acid is reacted with SDS for about 40 minutes and the optimized restriction enzyme is NlaIII.

B22. The method of any one of embodiments B1 to B21, wherein the one or more reagents that compartmentalize the proximity ligated nucleic acid molecules comprise a microfluidic compartmentalization device that produces microfluidic droplets.

B23. The method of any one of embodiments B1 to B21, wherein the one or more reagents that compartmentalize the proximity ligated nucleic acid molecules comprise microtiter plate wells into which complexes are diluted.

B24. The method of any one of embodiments B1 to B23, wherein a barcode is integrated into the compartmentalized nucleic acid during a nucleic acid amplification reaction.

B24.1. The method of any one of embodiments B1 to B23, wherein the compartmentalized nucleic acid is amplified in an amplification reaction and barcodes are ligated onto the amplified nucleic acid.

B25. The method of any one of embodiments B1 to B23, wherein the compartmentalized nucleic acid is fragmented and barcode oligonucleotides are attached by primer extension polymerization (PEP) for production of barcoded templates nucleic.

B26. The method of embodiment B25, wherein use of an optimized restriction enzyme to generate proximity ligated molecules produces a greater percent of compartmentalized nucleic acid molecules attached to barcode oligonucleotides compared to when an optimized restriction enzyme is not used.

B27. The method of embodiment B26, wherein the optimized restriction enzyme is NlaIII.

B28. The method of embodiment B26, wherein use of an optimized restriction enzyme to generate proximity ligated molecules produces a greater percent of compartmentalized nucleic acid molecules attached to barcode oligonucleotides compared to when a DpnII restriction enzyme or an equivalent enzyme is used.

B29. The method of any one of embodiments B26 to B28, wherein the primer extension polymerization (PEP) is for a period of 3 hours or greater.

B30. The method of embodiment B29, wherein the primer extension polymerization (PEP) is for a period of 6 hours or greater.

B31. The method of any one of embodiments B25 to B30, wherein the primer extension polymerization (PEP) comprises random primers.

B32. The method of any one of embodiments B1 to B23, wherein the compartmentalized nucleic acid is fragmented and barcode oligonucleotides are attached using a transposon with a uniquely barcoded oligonucleotide and a transposase.

B33. The method of embodiment B32, wherein the transposase is Tn5.

B34. The method of any one of embodiments B1 to B23, wherein the compartmentalized nucleic acid is fragmented and the barcode oligonucleotides are attached to the fragmented nucleic acid by ligation.

B35. The method of any one of embodiments B25 to B30, wherein the compartmentalized nucleic acid is enriched for a specific target by primer extension polymerization (PEP) comprising primers that specifically hybridize to specific target polynucleotides in the compartmentalized nucleic acid.

B36. The method of any one of embodiments B1 to B34, wherein the barcoded templates are enriched for a specific target polynucleotide.

B37. The method of embodiment B36, wherein barcoded templates are enriched by affinity purification.

B38. The method of embodiment B37, wherein the affinity purification comprises an affinity purification molecule attached to a target specific oligonucleotide that hybridizes to the target specific polynucleotide.

B39. The method of any one of embodiments B35 to B38, wherein the specific target polynucleotide comprises a locus or portion thereof.

B40. The method of any one of embodiments B35 to B38, wherein the specific target polynucleotide comprises a gene or portion thereof.

B41. The method of any one of embodiments B35 to B38, wherein the specific target polynucleotide comprises an exome or portion thereof.

B42. The method of any one of embodiments B1 to B41, comprising sequencing the barcoded templates using a sequencer that generates sequence reads of about 2 kilobases or greater.

B43. The method of any one of embodiments B1 to B41, comprising sequencing the barcoded templates using a sequencer that generates sequence reads of about 500 bases or less.

B44. The method of embodiment B42 or B43, wherein the sequence reads are generated at a sequencing depth of 30× or less.

B44.1. The method of any one of embodiments B42 to B44, comprising determining spatial-proximal contiguity information based on sequence reads containing a ligation junction.

B45. The method of any one of embodiments B42 to B44.1, comprising determining contiguity information based on sequence reads containing a ligation junction and sequence reads of barcode sequences in the barcode oligonucleotides.

B46. The method of any one of embodiments B42 to B45, comprising determining contiguity information based on identifying common barcode sequences in the barcode oligonucleotides and identifying chimeric sequences.

B47. The method of embodiment B46, comprising analyzing barcode sequences in the barcode oligonucleotides and chimeric sequences using a chimeric-aware assembly algorithm.

B48. The method of any one of embodiments B45 to B47, comprising determining haplotype information for the isolated nucleic acid using the contiguity information.

B49. The method of any one of embodiments B45 to B47, comprising determining ordering and orientation of contigs for the isolated nucleic acid using the contiguity information.

B50. The method of any one of embodiments B45 to B47, comprising determining deconvolution of a mixture of genomes for the isolated nucleic acid using the contiguity information.

B51. The method of any one of embodiments B45 to B47, comprising determining conformation and folding patterns of the isolated nucleic acid using the contiguity information.

B52. The method of any one of embodiments B45 to B47, comprising determining genomic variants of the isolated nucleic acid using the contiguity information.

B53. The method of embodiment B52, wherein the genomic variants comprise single nucleotide variants, insertions, deletion, inversions, translocations, and copy number variations, and other types of genome variants.

B54. The method of any one of embodiments B1 to B53, wherein the proximity ligated nucleic acid molecules are generated in situ.

B55. The method of any one of embodiments B1 to B53, wherein the proximity ligated nucleic acid molecules are generated in solution.

C1. A method for preparing library nucleic acid templates that preserves spatial-proximal and molecular contiguity, comprising:

reacting isolated nucleic acid with reagents that generate proximity ligated nucleic acid molecules;

preparing high molecular weight templates from the proximity ligated nucleic acid molecules, wherein the fraction of the templates that are long-cis templates is greater than 2%; and sequencing the templates using a sequencer that generates sequence reads of about 2 kilobases or greater.

C2. The method of embodiment C1, wherein the isolated nucleic acid comprises chromatin.

C3. The method of embodiment C1 or C2, wherein the isolated nucleic acid comprises substantially a whole genome or portions thereof.

C4. The method of any one of embodiments C1 to C3, wherein the isolated nucleic acid is obtained from cells.

C4.1. The method of any one of embodiments C1 to C3, wherein the isolated nucleic acid is from formalin-fixed paraffin-embedded cells, nuclei or nuclear matrix.

C5. The method of any one of embodiments C1 to C3, wherein the isolated nucleic acid is obtained from nuclei.

C6. The method of any one of embodiments C1 to C3, wherein the isolated nucleic acid is obtained from a nuclear matrix.

C7. The method of any one of embodiments C1 to C6, wherein the proximity ligated nucleic acid molecules comprise nucleic acid molecules of 25 Kb or greater.

C7.1. The method of any one of embodiments C1 to C6, wherein the proximity ligated nucleic acid molecules comprise nucleic acid molecules greater than 60 Kb.

C8. The method of any one of embodiments C1 to C7.1, wherein fraction is greater than 5%.

C9. The method of embodiment C8, wherein the fraction is greater than 10%.

C10. The method of embodiment C9, wherein the fraction is greater than 15%.

C11. The method of embodiment C10, wherein the fraction is greater than 20%.

C12. The method of embodiment C11, wherein the fraction is greater than 25%.

C13. The method of any one of embodiments C1 to C12, wherein the reagents comprise a reagent that solubilizes chromatin and the isolated nucleic acid is reacted with the reagent for greater than 10 minutes, whereby solubility is optimized.

C14. The method of embodiment C13, wherein the reagent that solubilizes chromatin is sodium dodecyl sulfate (SDS).

C15. The method of embodiment C13 or C14, wherein the isolated nucleic acid is reacted with the reagent for greater than 10 minutes but less than 80 minutes.

C16. The method of any one of embodiments C13 to C15, wherein the isolated nucleic acid is reacted with the reagent for about 40 minutes.

C17. The method of any one of embodiments C1 to C12, wherein the reagents comprise a restriction enzyme that produces a greater fraction of templates that are long-cis templates relative to the restriction enzyme HindIII, DpnII, MboI or an equivalent restriction enzyme, whereby the restriction enzyme is optimized to preserve spatial-proximal contiguity.

C18. The method of embodiment C17, wherein the optimized restriction enzyme is NlaIII.

C19. The method of any one of embodiments C1 to C12, wherein the reagents comprise a reagent that solubilizes chromatin, the isolated nucleic acid is reacted with the reagent for greater than 10 minutes, whereby solubility is optimized and a restriction enzyme that produces a greater fraction of the templates that are long-cis templates relative to the restriction enzyme HindIII, DpnII, MboI or an equivalent restriction enzyme, whereby the restriction enzyme is optimized to preserve spatial-proximal contiguity.

C20. The method of embodiment C19, wherein the reagent that solubilizes chromatin is sodium dodecyl sulfate (SDS), the isolated nucleic acid is reacted with SDS for about 40 minutes and the optimized restriction enzyme is NlaIII.

C21. The method of any one of embodiments C1 to C20, wherein the sequence reads are generated at a sequencing depth of 30× or less.

C22. The method of any one of embodiments C1 to C21, comprising determining spatial-proximal contiguity information based on sequence reads containing a ligation junction.

C23. The method of embodiment C22, comprising determining haplotype information for the isolated nucleic acid using the contiguity information.

C24. The method of embodiment C22, comprising determining ordering and orientation of contigs for the isolated nucleic acid using the contiguity information.

C25. The method of embodiment C22, comprising determining deconvolution of a mixture of genomes for the isolated nucleic acid using the contiguity information.

C26. The method of embodiment C22, comprising determining conformation and folding patterns of the isolated nucleic acid using the contiguity information.

C27. The method of embodiment C22, comprising determining genomic variants of the isolated nucleic acid using the contiguity information.

C28. The method of embodiment C27, wherein the genomic variants comprise single nucleotide variants, insertions, deletion, inversions, translocations, and copy number variations, and other types of genome variants.

C29. The method of any one of embodiments C1 to C28, wherein the proximity ligated nucleic acid molecules are generated in situ.

C30. The method of any one of embodiments C1 to C28, wherein the proximity ligated nucleic acid molecules are generated in solution.

D1. A method for preparing isolated nucleic acid that preserves spatial-proximal contiguity information, comprising:
reacting isolated nucleic acid with reagents that generate proximity-ligated nucleic acid molecules, whereby templates prepared from the proximity-ligated nucleic acid molecules have a fraction of long-cis templates greater than 2%.

D2. The method of embodiment D1, wherein the isolated nucleic acid comprises chromatin.

D3. The method of embodiment D1 or D2, wherein the isolated nucleic acid comprises substantially a whole genome or portions thereof.

D4. The method of any one of embodiments D1 to D3, wherein the isolated nucleic acid is obtained from cells.

D4.1. The method of any one of embodiments D1 to D3, wherein the isolated nucleic acid is from formalin-fixed paraffin-embedded cells, nuclei or nuclear matrix.

D5. The method of any one of embodiments D1 to D3, wherein the isolated nucleic acid is obtained from nuclei.

D6. The method of any one of embodiments D1 to D3, wherein the isolated nucleic acid is obtained from a nuclear matrix.

D7. The method of any one of embodiments D1 to D6, wherein the proximity ligated nucleic acid molecules comprise nucleic acid molecules of 25 Kb or greater.

D7.1. The method of any one of embodiments D1 to D6, wherein the proximity ligated nucleic acid molecules comprise nucleic acid molecules greater than 60 Kb.

D8. The method of any one of embodiments D1 to D7.1, wherein fraction is greater than 5%.

D9. The method of embodiment D8, wherein the fraction is greater than 10%.

D10. The method of embodiment D9, wherein the fraction is greater than 15%.

D11. The method of embodiment D10, wherein the fraction is greater than 20%.

D12. The method of embodiment D11, wherein the fraction is greater than 25%.

D13. The method of any one of embodiments D1 to D12, wherein the reagents comprise a reagent that solubilizes chromatin and the isolated nucleic acid is reacted with the reagent for greater than 10 minutes, whereby solubility is optimized.

D14. The method of embodiment D13, wherein the reagent that solubilizes chromatin is sodium dodecyl sulfate (SDS).

D15. The method of embodiment D13 or D14, wherein the isolated nucleic acid is reacted with the reagent for greater than 10 minutes but less than 80 minutes.

D16. The method of any one of embodiments D13 to D15, wherein the isolated nucleic acid is reacted with the reagent for about 40 minutes.

D17. The method of any one of embodiments D1 to D12, wherein the reagents comprise a restriction enzyme that produces a greater fraction of templates that are long-cis templates relative to the restriction enzyme HindIII, DpnII, MboI or an equivalent restriction enzyme, whereby the restriction enzyme is optimized to preserve spatial-proximal contiguity.

D18. The method of embodiment D17, wherein the optimized restriction enzyme is NlaIII.

D19. The method of any one of embodiments D1 to D12, wherein the reagents comprise a reagent that solubilizes chromatin and the isolated nucleic acid is reacted with the reagent for greater than 10 minutes, whereby solubility is optimized and a restriction enzyme that produces a greater fraction of the templates that are long-cis templates relative to the restriction enzyme HindIII, DpnII, MboI or an equivalent restriction enzyme, whereby the restriction enzyme is optimized to preserve spatial-proximal contiguity.

D20. The method of embodiment D19, wherein the reagent that solubilizes chromatin is sodium dodecyl sulfate (SDS), the isolated nucleic acid is reacted with SDS for about 40 minutes and the optimized restriction enzyme is NlaIII.

D21. The method of any one of embodiments D1 to D20, wherein the proximity ligated nucleic acid molecules are generated in situ.

D22. The method of any one of embodiments D1 to D20, wherein the proximity ligated nucleic acid molecules are generated in solution.

E1. A method for attaching barcode oligonucleotides to proximity-ligated nucleic acid molecules, comprising:
preparing proximity ligated nucleic acid molecules using an optimized restriction enzyme, wherein an optimized restriction enzyme produces a greater fraction of templates of the proximity-ligated nucleic acid molecules that are long-cis templates relative to the use of the restriction enzyme HindIII, DpnII or equivalent restriction enzymes; and fragmenting and attaching barcode oligonucleotides to the proximity-ligated nucleic acid molecules by a primer extension polymerization (PEP) reaction of greater than 3 hours in duration to produce barcoded templates, whereby a greater percent of templates have attached barcode oligonucleotides compared to when an optimized restriction enzyme is not used and the duration of the PEP reaction is 3 hours or less.

E2. The method of embodiment E1, wherein the optimized restriction enzyme is NlaIII.

E3. The method of embodiment E1 or E2, wherein the primer extension polymerization (PEP) is for a period of 6 hours or greater.

E4. The method of any one of embodiments E1 to E3, wherein the proximity ligated nucleic acid molecules are generated in situ.

E5. The method of any one of embodiments E1 to E3, wherein the proximity ligated nucleic acid molecules are generated in solution.

Certain embodiments of the technology are set forth in the claim(s) that follow(s).

What is claimed is:

1. A method for preparing library nucleic acid templates, comprising:

reacting isolated nucleic acid with one or more first reagents that generate proximity ligated nucleic acid molecules; and reacting the proximity ligated nucleic acid molecules with one or more second reagents that fragment and attach barcode oligonucleotides to the proximity ligated nucleic acid molecules thereby providing barcoded templates that are in virtual compartments, wherein the virtual compartments are not physically barred from intermixing with other virtual compartments, and wherein the barcode oligonucleotides attached to the barcoded templates in one of the virtual compartments are distinguishable from the barcode oligonucleotides attached to the barcoded templates in other virtual compartments and barcodes in the barcode oligonucleotides preserve molecular contiguity information for proximity ligated molecules.

2. The method of claim 1, wherein the one or more second reagents are a transposon with a uniquely barcoded oligonucleotide and a transposase.

3. The method of claim 2, wherein the transposase is Tn5.

4. The method of claim 1, wherein the isolated nucleic acid comprises substantially a whole genome or portions thereof.

5. The method of claim 1, wherein the isolated nucleic acid is obtained from cells, nuclei or nuclear matrix.

6. The method of claim 1, wherein the isolated nucleic acid is from formalin-fixed paraffin-embedded cells, nuclei or nuclear matrix.

7. The method of claim 1, wherein the proximity ligated nucleic acid molecules comprise nucleic acid molecules greater than 10 Kb, greater than 25 Kb or greater than 60 Kb.

8. The method of claim 1, wherein the fraction of the barcoded templates that are long-cis templates is greater than 2%, greater than 5%, greater than 10%, greater than 15%, greater than 20% or greater than 25%.

9. The method of claim 1, wherein the isolated nucleic acid is obtained using a reagent that solubilizes chromatin and the chromatin is reacted with the reagent for greater than 10 minutes but less than 80 minutes.

10. The method of claim 9, wherein the reagent that solubilizes chromatin is sodium dodecyl sulfate (SDS) and the chromatin is reacted with the SDS for about 40 minutes.

11. The method of claim 1, wherein the one or more first reagents comprise a restriction enzyme optimized to preserve spatial-proximal contiguity.

12. The method of claim 11, wherein the optimized restriction enzyme is NlaIII.

13. The method of claim 1, comprising sequencing the barcoded templates using a sequencer that generates sequence reads of about 500 base pairs or less.

14. The method of claim 13, comprising determining spatial proximal contiguity information for the isolated nucleic acid based on sequence reads containing a ligation junction and determining molecular contiguity for the isolated nucleic acid from sequence reads of barcode sequences in the barcode oligonucleotides.

15. The method of claim 14, comprising using the contiguity information of the isolated nucleic acid to determine haplotype phase information, to determine the order and orientation of contigs, for deconvolution of a mixture of genomes, to determine spatial conformation, topology and folding patterns, to inform de novo genome assembly, or to identify genomic variants comprising single nucleotide variants, insertions, deletion, inversions, translocations, copy number variations and other types of genome variants or combinations thereof.

16. The method of claim 1, wherein the proximity ligated nucleic acid molecules are generated in situ.

17. The method of claim 1, wherein the proximity ligated nucleic acid molecules are generated ex situ (in solution).

18. The method of claim 1, wherein the isolated nucleic acid is obtained by reacting chromatin with SDS for about 40 minutes, and the first set of reagents comprise the restriction enzyme NlaIII.

* * * * *

UNITED STATES PATENT AND TRADEMARK OFFICE
CERTIFICATE OF CORRECTION

PATENT NO. : 11,873,481 B2
APPLICATION NO. : 16/764787
DATED : January 16, 2024
INVENTOR(S) : Siddarth Selvaraj et al.

It is certified that error appears in the above-identified patent and that said Letters Patent is hereby corrected as shown below:

On the Title Page

In item (71), the Applicant section should read:
(71) Applicant: ARIMA GENOMICS, INC., Carlsbad, CA (US)

Signed and Sealed this
Fifth Day of March, 2024

Katherine Kelly Vidal
*Director of the United States Patent and Trademark Office*